(12) United States Patent
Zhang et al.

(10) Patent No.: US 8,057,829 B2
(45) Date of Patent: Nov. 15, 2011

(54) METHODS FOR REPELLING INSECTS USING SESQUITERPENE HYDROCARBONS AND THEIR DERIVATIVES

(75) Inventors: Qinghe Zhang, Spokane Valley, WA (US); Armenek Margaryan, Spokane Valley, WA (US); Rodney G. Schneidmiller, Greenacres, WA (US)

(73) Assignee: Sterling International Inc., Spokane, WA (US)

( * ) Notice: Subject to any disclaimer, the term of this patent is extended or adjusted under 35 U.S.C. 154(b) by 0 days.

(21) Appl. No.: 12/346,082

(22) Filed: Dec. 30, 2008

(65) Prior Publication Data

US 2010/0166896 A1 Jul. 1, 2010

(51) Int. Cl.
 *A01N 65/00* (2009.01)
(52) U.S. Cl. ..................................................... 424/725
(58) Field of Classification Search .................. None
 See application file for complete search history.

(56) References Cited

U.S. PATENT DOCUMENTS

| | | |
|---|---|---|
| 4,049,828 A | 9/1977 | Cole |
| 4,992,270 A | 2/1991 | Wilson |
| 5,030,739 A | 7/1991 | Foricher |
| 5,227,406 A | 7/1993 | Beldock |
| 5,314,693 A | 5/1994 | Suga |
| 5,346,922 A | 9/1994 | Beldock |
| 5,621,013 A | 4/1997 | Beldock |
| 5,648,398 A | 7/1997 | Beldock |
| 6,352,702 B1 | 3/2002 | Ryan |
| 6,352,703 B1 | 3/2002 | Henderson |
| 6,548,085 B1 | 4/2003 | Zobitne |
| 6,734,159 B2 | 5/2004 | Pickenhagen |
| 6,762,157 B1 | 7/2004 | Babinski |
| 7,259,135 B2 * | 8/2007 | Markert et al. ............ 512/27 |
| 7,311,923 B2 | 12/2007 | Tsubouchi |
| 7,378,557 B1 | 5/2008 | Zhang |
| 7,381,431 B2 | 6/2008 | Baker |
| 2001/0043937 A1 | 11/2001 | Baker |
| 2002/0040167 A1 | 4/2002 | Pickenhagen |
| 2002/0160035 A1 | 10/2002 | Fotinos |
| 2003/0138471 A1 | 7/2003 | Coats |
| 2003/0166974 A1 | 9/2003 | Pickenhagen |
| 2004/0223998 A1 | 11/2004 | Iyer |
| 2004/0242936 A1 | 12/2004 | Jasra |
| 2005/0147640 A1 | 7/2005 | Sexton |
| 2006/0134239 A1 | 6/2006 | Weide |
| 2006/0257441 A1 | 11/2006 | Komai |
| 2007/0078071 A1 | 4/2007 | Lee |
| 2007/0098750 A1 | 5/2007 | Bessette |
| 2007/0141011 A1 | 6/2007 | Lehn |
| 2007/0172463 A1 | 7/2007 | Martin |
| 2007/0224232 A1 | 9/2007 | Sherwood |
| 2008/0020078 A1 | 1/2008 | Enan |
| 2008/0057005 A1 | 3/2008 | Lehn |
| 2008/0069785 A1 | 3/2008 | Jones |
| 2008/0075796 A1 | 3/2008 | Enan |
| 2008/0155886 A1 | 7/2008 | Okuda |
| 2008/0201796 A1 | 8/2008 | Chappell |
| 2008/0269177 A1 | 10/2008 | Bessette |

FOREIGN PATENT DOCUMENTS

| | | | |
|---|---|---|---|
| JP | 2002308705 A | | 10/2002 |
| JP | 2004051564 | * | 2/2004 |
| JP | 2004099535 | * | 4/2004 |
| WO | 0027197 A1 | | 5/2000 |

OTHER PUBLICATIONS

Nature's Lather, 2 pages, 2009.*
Da Silva, T.B.C, et al., "Chemical Constituents and Preliminary Antimalarial Activity of Humiria balsamifera," Pharmaceutical Biology 42(2):94-97, Apr. 2004.
Flint, H.M, et al., "Caryophyllene: an Attractant for the Green Lacewing," Environmental Entomology 8(6):1123-1125, Dec. 1979.
Klun, J.A., and M. Debboun, "A New Module for Quantitative Evaluation of Repellent Efficacy Using Human Subjects," Journal of Medical Entomology 37(1):177-181, 2000.
Kuo, P.-M., et al., "Insecticidal Activity of Essential Oil From Chamaecyparis formosensis Matsum," Holzforschung, 61(5):595-599, Aug. 2007.
North, R.D. et al., "Agonistic Behavor of the Leaf-Cutting Ant Atta sexdens rubropilosa Elicited by Caryophyllene," Journal of Insect Behavior 13(1):1-13, 2000.
Zhang, A., et al., "A Natural Bridged Tricyclic Sesquiterpene, Isolongifolenone, is a Repellent Against Blood-Feeding Arthropods," Poster shown at Entomological Society of America Annual Meeting, San Diego, Calif., Dec. 9-12, 2007, <http://esa.confex.com/esa/2007/techprogram/paper_32705.htm>, retrieved Jun. 15, 2009.
Zhang, Q.-H., et al., Bark Volatiles from Nonhost Angiosperm Trees of Spruce Bark Beetle, Ips typographus (L.) (Coleoptera: Scolytidae): Chemical and Electrophysiological Analysis, Chemoecology 10:69-80, 2000.

* cited by examiner

*Primary Examiner* — Michael Meller
(74) *Attorney, Agent, or Firm* — Christensen, O'Connor, Johnson Kindness PLLC

(57) ABSTRACT

Methods for repelling flying or biting insects from an area, a human, or an animal subject are provided. The methods include treating the area, or applying to a subject or to a device worn by the subject seychellene, α-guaiene, and α-bulnesene, or a mixture thereof. Additional compounds including β-caryophyllene, isocaryophyllene, β-caryophyllene oxide, β-caryophyllene ketone, α-humulene, β-patchoulene, α-patchoulene, β-elemene, (+)-longipinene, (−)-isolongifolene, (+)-longifolene, and linalool, clove oil, and/or patchouli oil may also be used.

5 Claims, 14 Drawing Sheets

METHODS FOR REPELLING INSECTS USING SESQUITERPENE HYDROCARBONS AND THEIR DERIVATIVES

BACKGROUND

Insects in the order *Diptera* include many familiar flying insects such as filth and biting flies and mosquitoes. Many species of *Diptera* are known as vectors for varieties of diseases in man, other animals, and plants. For example, diseases such as dysentery, cholera, and yaws may be transmitted on house flies' feet and mouthparts. Horse flies and deer flies are known to spread tularemia, loiasis, and trypanosomiasis. Black flies are known to spread human onchoceriasis and leucocytozoon infections of poultry. Sand flies are known to spread leishmaniasis. Mosquitoes are known to spread malaria, encephalitis, yellow fever, and filariasis. Accordingly, it is important to control flying or biting insects such as flies and mosquitoes, especially in less developed countries, to minimize and reduce the risk of these insects serving as vectors for diseases in humans.

Various chemicals and mixtures have been studied and used for insect repelling activities. For example, N,N-diethyl-m-toluamide (DEET), and dimethyl phthalate are widely used as insect repellents. DEET is very effective in protecting outdoor people from insects. Certain formulations containing DEET have been designed for cosmetic uses, for example, in sunscreen products such as lotions.

While DEET is an effective repellent, it is not particularly pleasing in smell, it stings when applied, and its use causes a number of harmful side effects in humans including injuries to eyes, mucous membranes, and sensitive skin. Because DEET is absorbed through the skin, toxic systemic reactions may result even when the compound is only used topically. Repeated exposure to DEET has been associated with incidences of seizures, irritability, confusion, insomnia, encephalopathy, and coma.

The potential hazards of using a product with DEET as an active ingredient indicate that there is a need for new methods for repelling insects.

SUMMARY

This summary is provided to introduce a selection of concepts in a simplified form, which are further described below in the Detailed Description. This summary is not intended to identify key features of the claimed subject matter, nor is it intended to be used as an aid in determining the scope of the claimed subject matter.

Methods are disclosed for repelling one or more insects from, but not limited to, the order *Diptera* and, in particular, for repelling filth flies, biting flies, and mosquitoes. In one aspect, a method for repelling an insect from an area is provided. The method comprises treating the area with at least one repellent compound selected from the group consisting of seychellene, α-guaiene, and α-bulnesene, or a mixture thereof. In another aspect, a method for repelling an insect from a human or animal subject is provided. The method comprises applying to a subject or to a device worn by the subject at least one repellent compound selected from the group consisting of seychellene, α-guaiene, and α-bulnesene, or a mixture thereof. In another aspect, a method for inhibiting or blocking the biting activity of a mosquito from a human or animal subject is provided. The method comprises applying to a subject or to a device worn by the subject at least one repellent compound selected from a group consisting of seychellene, α-guaiene and α-bulnesene, or a mixture thereof.

The methods above may further include one or more compounds selected from the group consisting of β-caryophyllene, isocaryophyllene, β-caryophyllene oxide, β-caryophyllene ketone, α-humulene, β-patchoulene, α-patchoulene, β-elemene, (+)-longipinene, (−)-isolongifolene, (+)-longifolene, and linalool. The methods may further include the use of clove oil, patchouli oil, or a mixture thereof.

Representative insects that may be repelled include filth flies, biting flies, blood feeding flies, mosquitoes, and other flying or biting insects, mostly from, but not limited to, the order *Diptera*. Filth flies refer to flies that belong primarily to the families Muscidae, Calliphoridae, and Sarcophagidae. Representative examples of filth flies include the house fly (*Musca domestica*), the black blow fly (*Phormia regina*), and bottle flies (*Calliphora* spp.). Blood feeding or biting flies refer to flies that include the family Tabanidae (horse flies), and include flies such as stable flies (*Stomoxys calcitrans*), horn flies (*Haematobia irritans*), and deer flies (*Chrysops* spp.). Black flies (family Simuliidae) and sand flies (family Psychodidae) are also included. Other insects that may be repelled using the methods disclosed herein include *Musca domestica* (a housefly), *Lucilia sericata* (a green bottle fly), *Sarcophaga* sp. (flesh flies), *Muscina stabulans* (a false stable fly), and *Phlebotomus papatasi* (a sand fly) and mosquitoes including *Aedes aegypti*, *Aedes increpitus*, *Anopheles stephensi*, *Anopheles gambiae*, and *Culex pipiens*.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
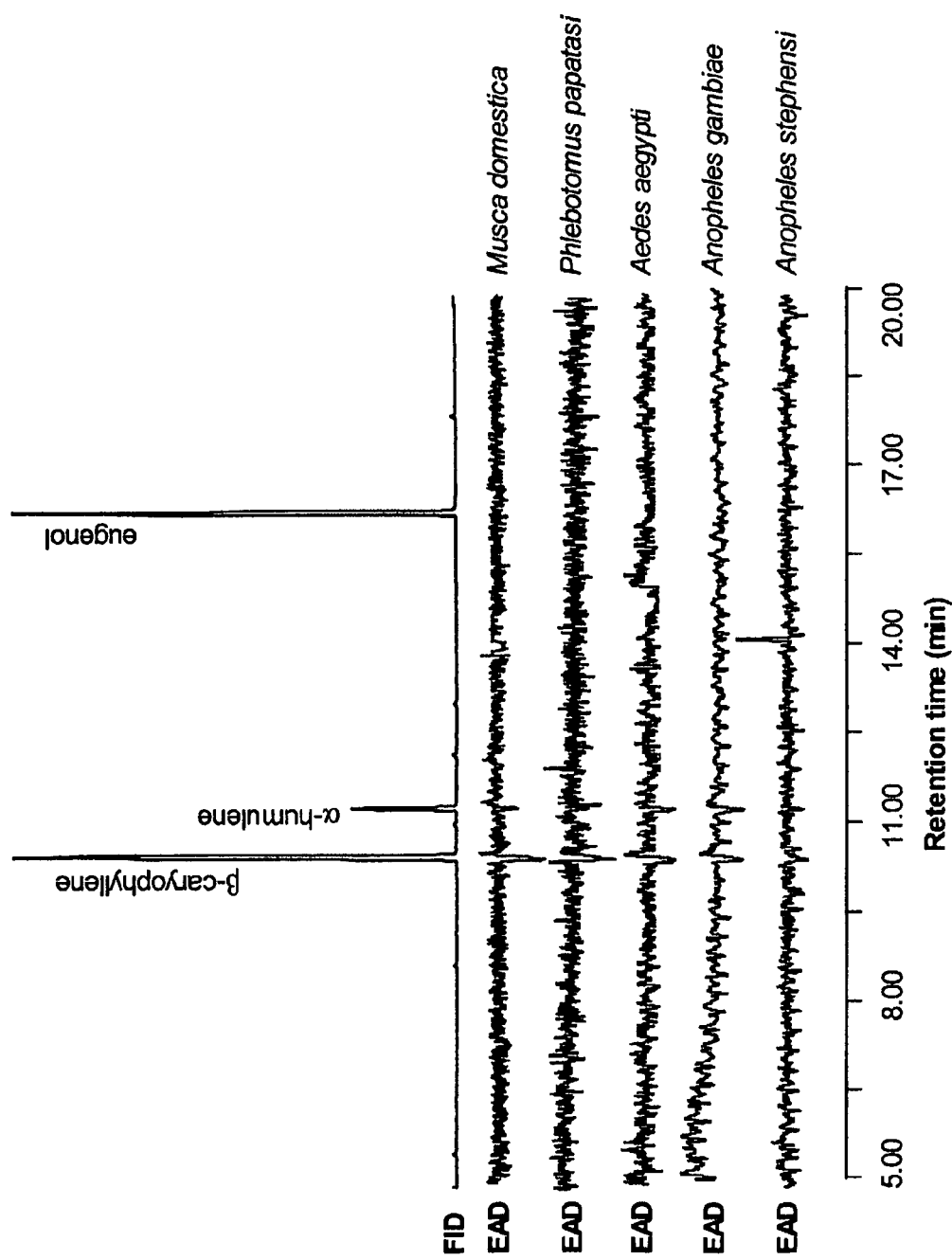
FIG. 1 shows the antennal responses of a female housefly, sand fly, and three species of mosquitoes to Solid Phase Microextraction (SPME: CAR/PDMS) samples of clove essential oil, recorded by a GC-flame ionization detector (FID) coupled with an electroantennographic detector (EAD)

Methods are disclosed for repelling an insect by using a sesquiterpene hydrocarbon compound or derivative of a sesquiterpene hydrocarbon compound. As used herein, the term "sesquiterpene hydrocarbon" refers to any linear or cyclic natural product with C15 skeletons constructed from three (3) five-carbon building-units. As used herein, the term "sesquiterpene hydrocarbon derivative" refers to any oxidized form of a sesquiterpene hydrocarbon compound, as defined herein. Representative oxidized forms include alcohol, oxide, ketone, aldehyde, carboxylic acid, lactone, ketal, and ester.

Methods are disclosed for repelling an insect of the order of Diptera from an area by treating the area with at least one repellent compound selected from the group consisting of seychellene, α-guaiene, and α-bulnesene, or a mixture thereof. These compounds occur naturally in patchouli oil. Patchouli oil is derived from several species of plants including Pogostemon cablin, for example. The compounds may be isolated in substantially pure form through well-known separation techniques, such as distillation.

In one embodiment, the repellent compound is seychellene. Seychellene is a tricyclic sesquiterpene that may be isolated from patchouli oil. Alternatively, synthesis of seychellene can be performed as described by Fukamiya, N.; Kato, M.; and Yoshikoshi, A., Chem. Commun. 1971, 1120. Seychellene is commonly used in perfume compositions and in flavoring compositions. Seychellene has the following structure:

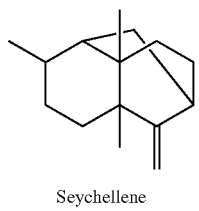

Seychellene

In one embodiment, the repellent compound is α-guaiene. Guaiene is a hydrocarbon sesquiterpene that may be isolated from patchouli oil. There are two guaiene isomers, α-Guaiene and β-Guaiene. Both structures are shown below. β-Guaiene is a known termite attractant from U.S. Pat. No. 6,352,703. However, α-Guaiene is disclosed herein as an insect repellent.

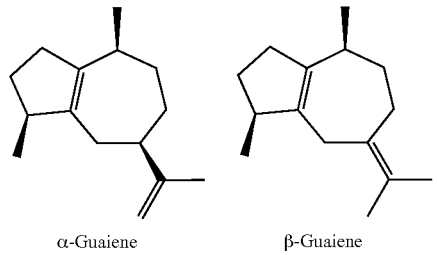

α-Guaiene     β-Guaiene

In one embodiment, the repellent compound is α-bulnesene. Bulnesene is a guaiene-type sesquiterpene, which may be isolated from patchouli oil. Bulnesene has two isomers, α-bulnesene and β-bulnesene. Both structures are shown below. α-Bulnesene is also known as δ-guaiene.

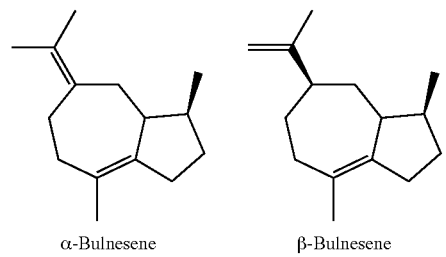

α-Bulnesene     β-Bulnesene

Other sesquiterpene hydrocarbons may be used together with seychellene, α-guaiene, and/or α-bulnesene and mixtures thereof for repelling insects of the order Diptera. Representative sesquiterpene hydrocarbons that are useful in combination with one or more of seychellene, α-guaiene, α-bulnesene and mixtures thereof include β-caryophyllene, isocaryophyllene, α-humulene, β-caryophyllene oxide, β-caryophyllene ketone, (+)-longifolene, (−)-isolongifolene, (+)-longipinene, β-patchoulene, α-patchoulene, and β-elemene. Linalool, although not a sesquiterpene, can be used in combination with other sesquiterpenes disclosed herein.

β-caryophyllene is a natural bicyclic sesquiterpene that is a constituent of some essential oils, especially clove oil and the oil from the stems and flowers of Syzygium aromaticum.

Isocaryophyllene is the cis double bond isomer of β-caryophyllene. It is believed that isocaryophyllene is mainly an artifact of the isolation process for β-caryophyllene.

α-Humulene is the open ring isomer of β-caryophyllene and is a naturally occurring monocyclic sesquiterpene. α-Humulene is found in the essential oils of Humulus lupulus (hops) from which it derives its name, and in clove oil. The structures of β-caryophyllene, isocaryophyllene, and α-Humulene are shown below.

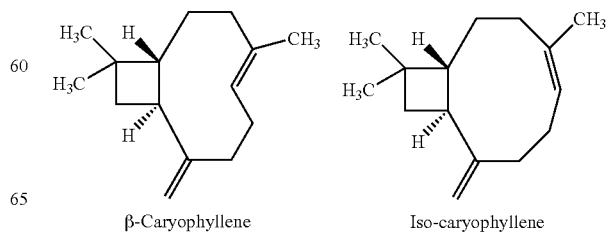

β-Caryophyllene     Iso-caryophyllene

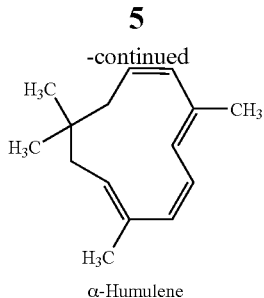

α-Humulene

β-Caryophyllene has a highly strained and reactive endocyclic trans-cyclononene ring, a trans-fused bicyclo [7.2.0]undecane skeleton, and a reactive cyclobutylvinyl moiety; all of which combine to account for its propensity to undergo facile structural rearrangements. Varieties of rearranged and oxidized forms of β-caryophyllene may be used as repellents for insects. Representative β-caryophyllene derivatives include oxides and ketones.

β-Caryophyllene ketones and isocaryophyllene ketones can be obtained by the functionalization of the exocyclic methylene group carried out in the presence of the endocyclic double bond, ozonolysis of β-caryophyllene epoxide, or deoxygenation and conversion of the 2- and 3-alcohol derivatives with high stereospecificity. Representative β-caryophyllene derived ketones include:

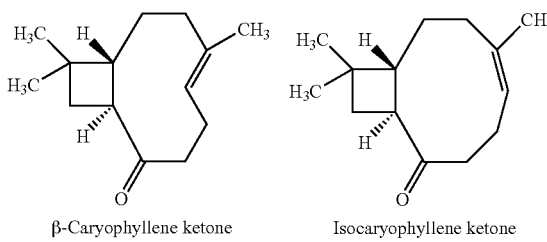

β-Caryophyllene ketone     Isocaryophyllene ketone

β-Caryophyllene oxide, shown below, can be obtained by oxidation of the double ring bond in P-caryophyllene.

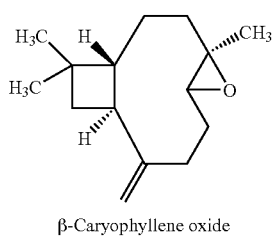

β-Caryophyllene oxide (+)-Longifolene, with the structure shown below, is the common chemical name of a naturally-occurring oily liquid hydrocarbon found primarily in the high-boiling fraction of certain pine resins. (+)-Longifolene is the main component of heavy turpentine oil in Chinese Masson's pine.

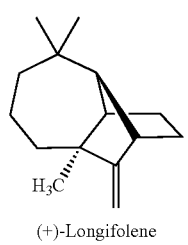

(+)-Longifolene

Chemically, (+)-longifolene is a tricyclic sesquiterpene. This molecule is chiral, and the enantiomer commonly found in pines and other higher plants exhibits a positive optical rotation of about +42.73°. The other enantiomer (optical rotation of about −42.73°) is found in small amounts in some primitive plants like fungi and liverworts.

(+)-Longifolene may be obtained by precise distillation of heavy turpentine oil or other essential oils, and is also commercially available. The purity of (+)-longifolene usually is in a range of 55 to 75%. The main impurities in the raw material are sesquiterpene hydrocarbons, such as β-caryophyllene.

(+)-Longifolene, as a tricyclic sesquiterpene in a high energy state, can be rearranged into various derivatives in the presence of a Lewis acid under different conditions. Representative (+)-longifolene derivatives include various isomers of (+)-longifolene and various oxidized derivatives of (+)-longifolene and its isomers.

(−)-Isolongifolene, with a structure shown below, is a well known isomer of (+)-longifolene. U.S. Patent Application Publication No. 2004/242936 describes an isomerization process to convert (+)-longifolene to (−)-isolongifolene (2,2,7, 7-tetramethyltricyclo undec-5-ene) using nano-crystalline sulfated zirconia as a solid super acid catalyst. Isolongifolenone can be made from (−)-isolongifolene as disclosed in U.S. Pat. No. 7,378,557.

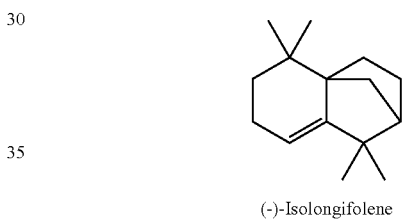

(−)-Isolongifolene (+)-Longipinene, with the structure shown below, is another sesquiterpene hydrocarbon in the longifolene family.

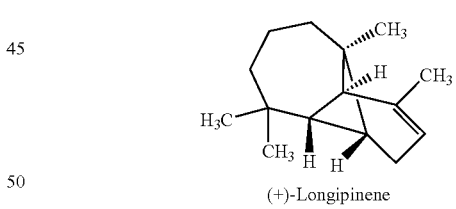

(+)-Longipinene

Patchoulene is a sesquiterpene hydrocarbon found in patchouli oil. There are two isomers, α-Patchoulene and β-Patchoulene, each having the structure as shown below.

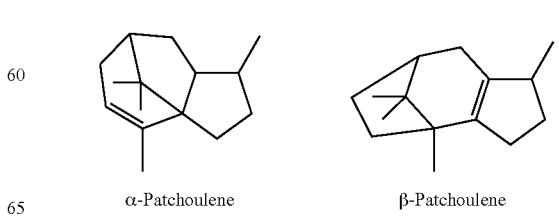

α-Patchoulene     β-Patchoulene

β-Elemene is a chemical compound that can be extracted from numerous plants including *Curcuma aromatia*, and *Curcuma longa linn* (all belonging to Ziniberaceae). β-Elemene has a structure as shown below.

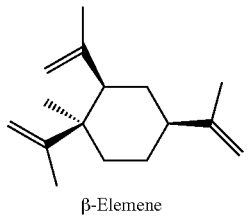

β-Elemene

Linalool, or 3,7-dimethyl-3-hydroxy-1,6-octadiene, is a naturally occurring terpene alcohol found in the essential oil of Coriander (*Coriandrum sativum*), Rosewood (*Aniba* spp.) and Ho oils (*Cinnamomum camphora* var. *linaloolifera* and *Cinnamomum camphora* var. *glavescens*). Commercial synthetic linalool has been prepared by isomerization of geraniol. The structure of linalool is shown below.

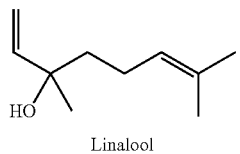

Linalool

The above-described sesquiterpene hydrocarbons, linalool, and the derivatives thereof, may be used in substantially pure form or may be combined with essential oils, such as clove oil and patchouli oil.

Clove oil is an essential oil from the clove plant, *Syzygium aromaticum*. The main chemical components of clove oil include eugenol, eugenol acetate, iso-eugenol, and β-caryophyllene. Patchouli oil may be extracted from *Pogostemon cablin* (also known as *Pogostemon patchouli*) of the Labiatae family and is also known as patchouly and puchaput. The chemical components of patchouli oil include β-patchoulene, α-guaiene, β-caryophyllene, α-patchoulene, seychellene, α-bulnesene, norpatchoulenol, patchouli alcohol, and pogostol.

The sesquiterpene hydrocarbons and their derivatives disclosed herein have been identified as suitable insect repellents by testing via a gas chromatographic-electroantennographic detection (GC-EAD) method as described in Example 1 below. This method can be used to efficiently screen for potentially behaviorally active compounds, including insect repellents, attractants, deterrents, or attraction-inhibitors from complex natural sources or synthetic mixtures. EAD activity shows that the insect has olfactory receptor neurons for the compound, which is an indicator that the compound may be an insect repellent if it comes from a natural repellent source (e.g., essential oils), or an attractant, if coming from an attractive natural source. Accordingly, if a compound shows EAD activity, the compound and any structurally-similar compound, including any isomer or oxidized derivative, may likewise be an insect repellent or attractant.

EAD-active sesquiterpenes from the repellent essential oils, clove oil and patchouli oil, include seychellene, α-guaiene, α-bulnesene, β-caryophyllene, isocaryophyllene, β-caryophyllene oxide, α-humulene, β-patchoulene, α-patchoulene, β-elemene, (+)-longipinene, (−)-isolongifolene, (+)-longifolene. The terpene alcohol linalool was also found to be EAD-active. The EAD activities of the above-mentioned compounds are detectable in one or more of the following insects: housefly (*Musca domestica* L.), green bottle fly (*Lucilia sericata*), flesh fly (*Sarcophaga* sp.), and false stable fly (*Muscina stabulans*); several mosquitoes such as *Culex pipiens, Aedes aegypti, Aedes increpitus, Anopheles gambiae, Anopheles stephensi*, and a sand fly (*Phlebotomus papatasi*).

The GC-EAD antennal response of a female housefly (*Musca domestica*), sand fly (*Phlebotomus papatasi*), and mosquitoes including the species *Aedes aegypti, Anopheles gambiae*, and *Anopheles stephensi* were tested with clove essential oil. FIG. 1 is a simultaneous recording of GC flame ionization detection (FID) and electroantennographic detection (EAD) of the insect antennae to solid phase microextraction (SPME: CAR/PDMS) samples of clove essential oil in a 20 ml glass vial for 20 sec. Two EAD-active compounds, β-caryophyllene and α-humulene, and one EAD-inactive (or weakly active) compound, eugenol, were identified by GC-MS, and confirmed with synthetic standards. As shown in FIG. 1, two of the three major compounds detected from the SPME sample of the clove essential oil, β-caryophyllene and α-humulene, elicited antennal responses by one or more of the housefly, sand fly, and mosquitoes *Aedes aegypti, Anopheles gambiae*, and *Anopheles stephensi*, while the third major component, eugenol, was antennally inactive at the dose tested. No detectable EAD activities from the housefly, sand fly, or mosquitoes were found in reaction to any minor components of the clove oil SPME samples.

Figure 2:
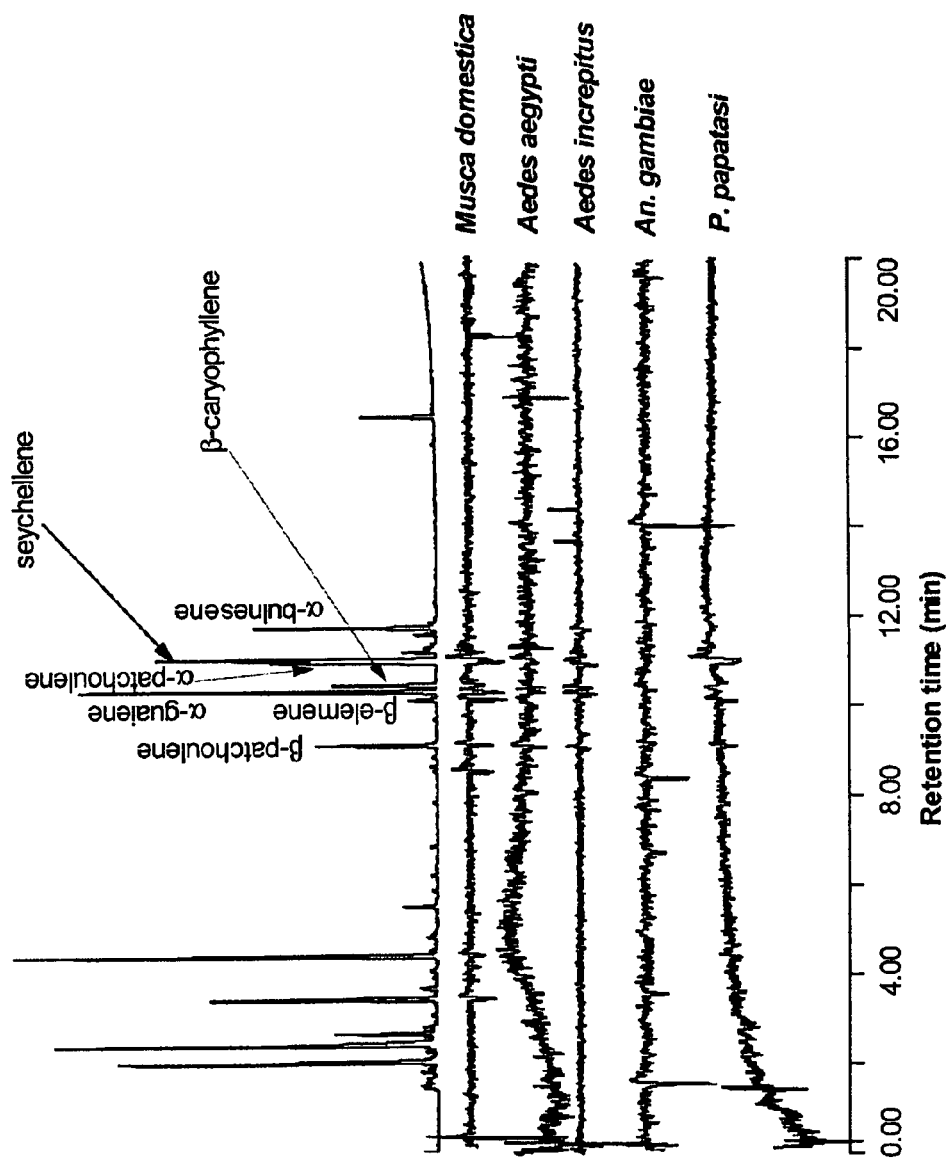
FIG. 2 shows GC-EAD responses of a female housefly, sand fly, and three species of mosquito antennae to SPME (CAR/PDMS) samples of patchouli oil, containing α-patchoulene, β-patchoulene, β-elemene, seychellene, α-guaiene, α-bulnesene, and β-caryophyllene.

FIG. 2 shows GC-EAD antennal responses of a female housefly, sand fly, and mosquitoes (*Aedes aegypti, Aedes increpitus*, and *Anopheles gambiae*) to SPME (CAR/PDMS) samples of patchouli essential oil. Seven major sesquiterpenes, α-patchoulene, β-patchoulene, β-elemene, seychellene, α-guaiene, α-bulnesene, and β-caryophyllene, elicited EAD-activity by one or more of the housefly, sand fly, and mosquito antennae. These EAD-active compounds were identified by GC-MS.

Figure 3:
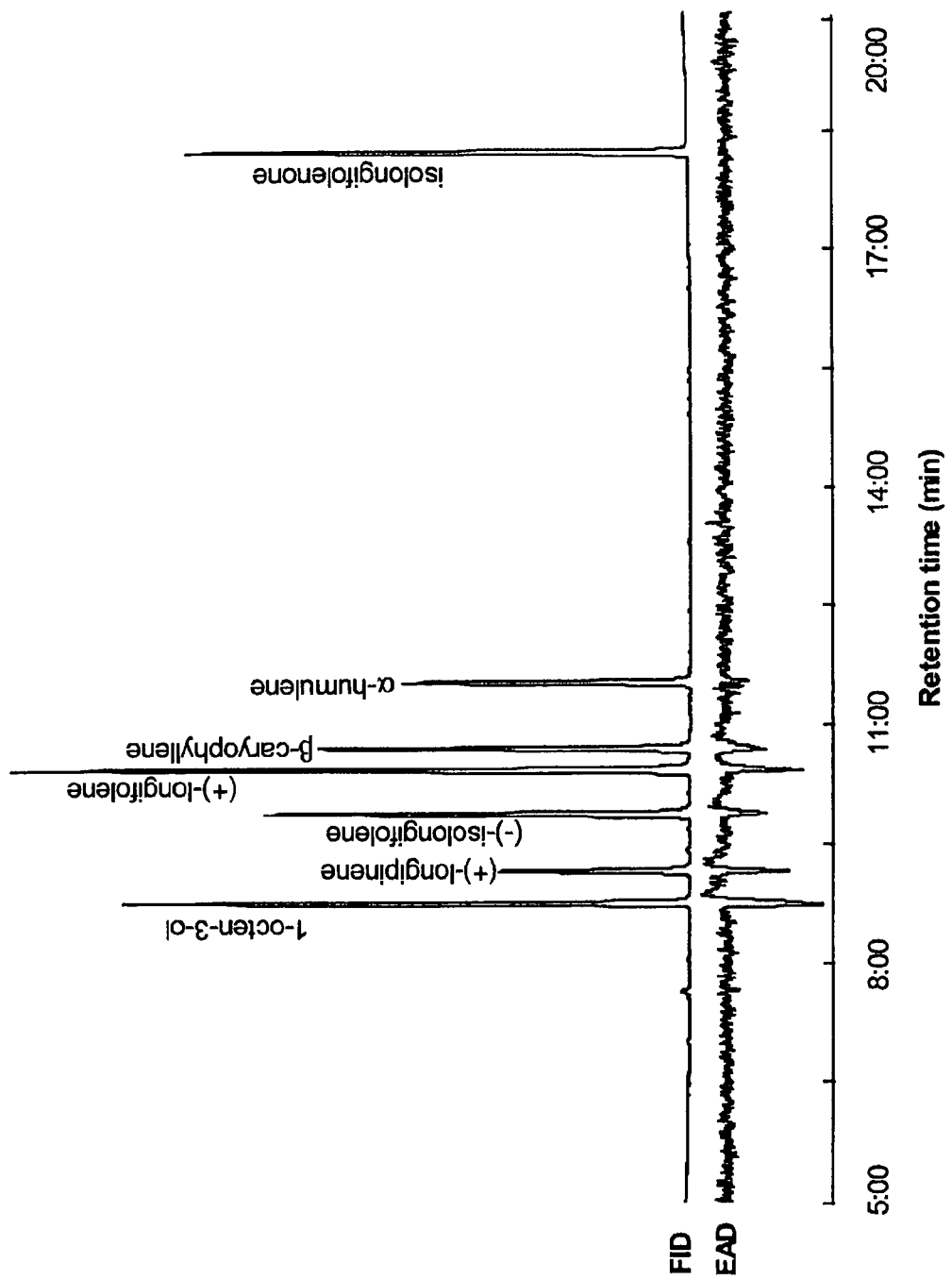
FIG. 3 shows GC-EAD responses of the female housefly antenna to a synthetic mixture of 1-octen-3-ol, (+)-longipinene, (−)-isolongifolene, (+)-longifolene, β-caryophyllene, α-humulene, and isolongifolenone.

The GC-EAD responses of the female housefly antenna were tested on a synthetic mixture of 1-octen-3-ol, a known attractant used as a positive control, and representative sesquiterpene hydrocarbons and derivatives, (+)-longipinene, (−)-isolongifolene, (+)-longifolene, β-caryophyllene, α-humulene, and isolongifolenone, with about 100 ng of each compound in the mixture. As shown in FIG. 3, the sesquiterpene hydrocarbons, (+)-longipinene, (−)-isolongifolene, (+)-longifolene, β-caryophyllene and α-humulene were active on housefly antennae, while isolongifolenone (a sesquiterpene ketone) was inactive at the dose tested.

Figure 4:
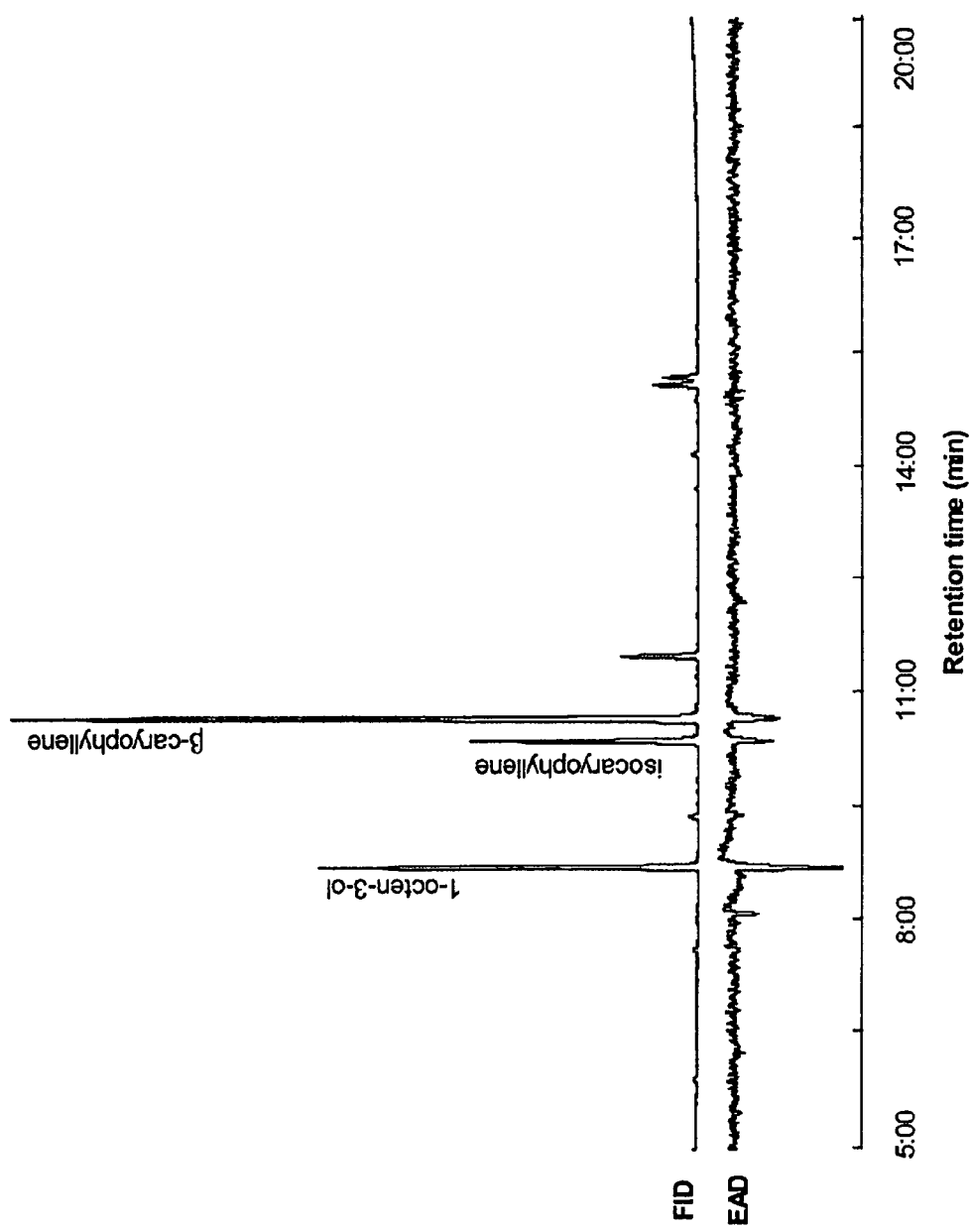
FIG. 4 shows the GC-EAD responses of the male housefly antenna to a synthetic mixture of 1-octen-3-ol, β-caryophyllene, and isocaryophyllene.

The GC-EAD responses of the male housefly antenna were tested on a synthetic mixture of 1-octen-3-ol, and two representative sesquiterpenes, β-caryophyllene and isocaryophyllene, with about 100 ng of each compound in the mixture. As shown in FIG. 4, both β-caryophyllene and its cis-isomer, isocaryophyllene were EAD-active.

Figure 5:
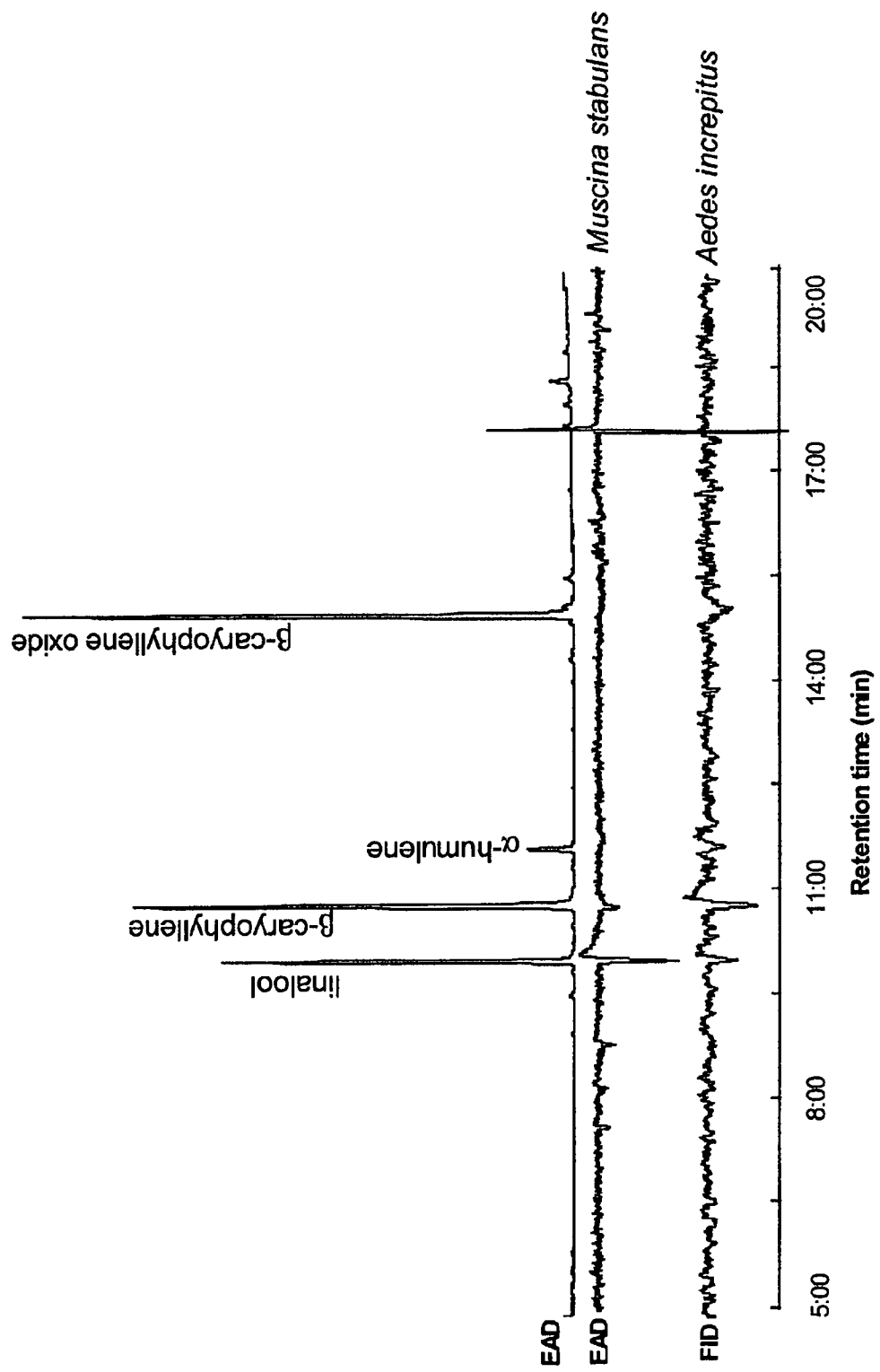
FIG. 5 shows the GC-EAD responses of the male false stable fly and the female mosquito *Aedes* (*Ochlerotatus*) *increpitus* Dyar antennae to a synthetic mixture of linalool, β-caryophyllene, α-humulene, and β-caryophyllene oxide.

The GC-EAD responses of the male false stable fly *Muscina stabulans* antenna and the female mosquito *Aedes* (*Ochlerotatus*) *increpitus* Dyar antenna were tested on a synthetic mixture of linalool and two representative sesquiterpene hydrocarbons, β-caryophyllene and α-humulene, and one sesquiterpene oxide, β-caryophyllene oxide, with about 100 ng of each compound in the mixture. The results are shown in FIG. 5. The compounds tested appear to be active on at least one of the insects tested.

Figure 6:
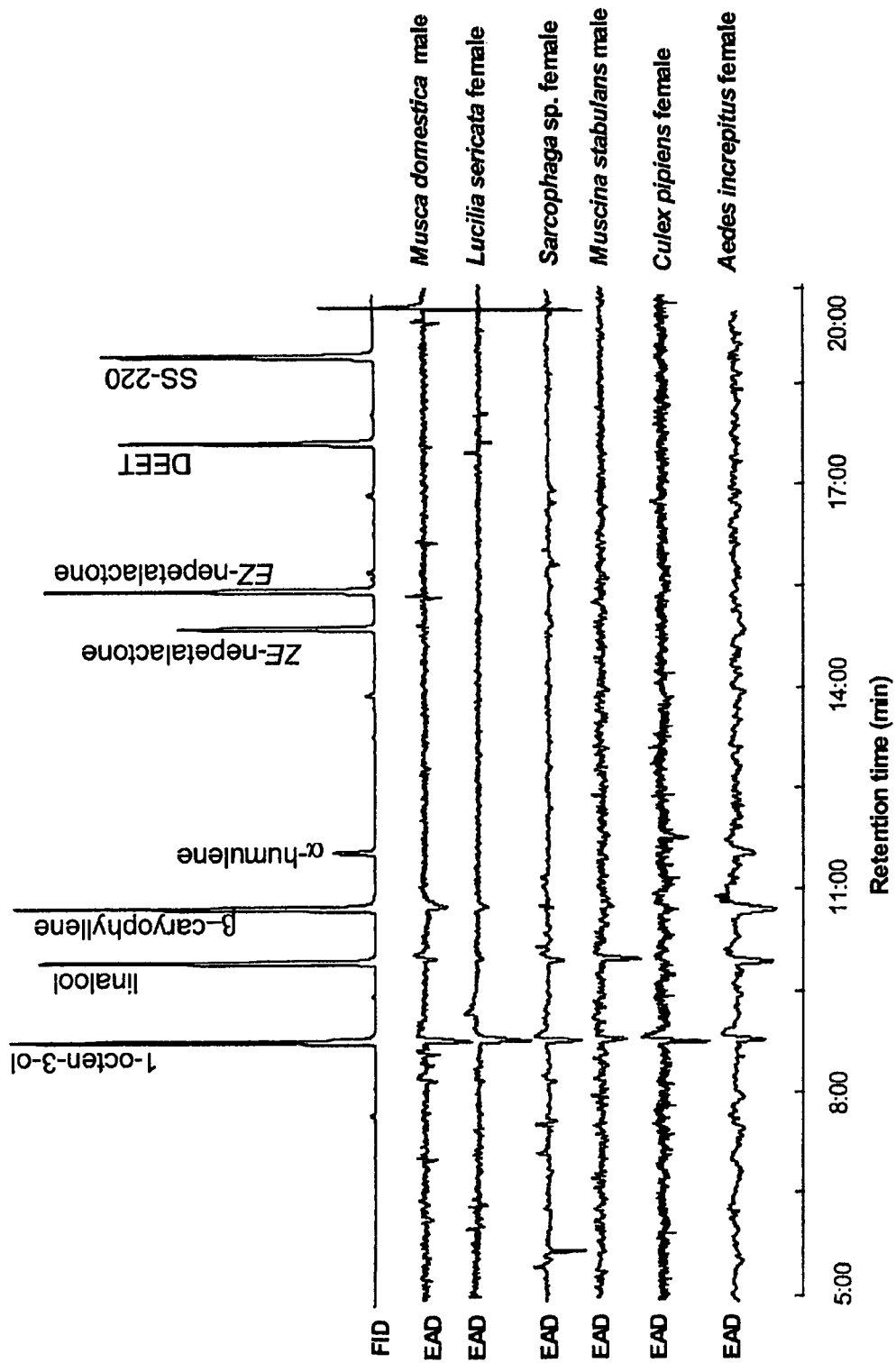
FIG. 6 shows the GC-EAD responses of a male house fly, female green bottle fly, female flesh fly, male false stable fly and two species of mosquitoes to a synthetic mixture of 1-octen-3-ol, linalool β-caryophyllene, α-humulene, ZE-nepetalactone, EZ-nepetalactone, DEET, and SS220.

The GC-EAD responses of several species of flies and two species of mosquito antennae were tested on a synthetic mixture of 1-octen-3-ol, linalool, two representative sesquiterpene hydrocarbons, β-caryophyllene and α-humulene, ZE-nepetalactone, EZ-nepetalactone, and two known insect repellents, DEET, and SS220, with about 100 ng of each compound in the mixture. DEET and SS220 are used as positive controls in the experiment. The compound 1-octen-3-ol is a known attractant for the insects and is also used as a positive control. The insects tested are species of *Musca domestica, Lucillia sericata, Sarcophaga* sp., *Muscina stabulans, Culex pipiens*, and *Aedes increpitus*. The results are shown in FIG. 6. The sesquiterpenes β-caryophyllene and α-humulene, and linalool appear to be active on at least one of the insects tested.

As shown in FIGS. 5 and 6, antennae of at least one of *Muscina stabulans, Aedes increpitus, Culex pipiens, Musca domestica, Lucilia sericata*, and *Sarcophaga* sp. responded to at least one of β-caryophyllene, α-humulene, β-caryophyllene oxide and linalool.

The GC-EAD responses of the female mosquito *Culex pipiens* antenna were tested on a synthetic mixture of 1-octen-3-ol, and two sesquiterpene hydrocarbons, β-caryophyllene and isocaryophyllene, with about 100 ng of each compound in the mixture. The results are shown in FIG. 7.

The GC-EAD responses of the female mosquito *Culex pipiens* antenna were tested on a synthetic mixture of 1-octen-3-ol, and representative sesquiterpene hydrocarbons and derivatives including (+)-longipinene, (−)-isolongifolene, (+)-longifolene, β-caryophyllene, and isolongifolenone, with about 100 ng of each compound in the mixture. The results are shown in FIG. 8.

Figure 7:
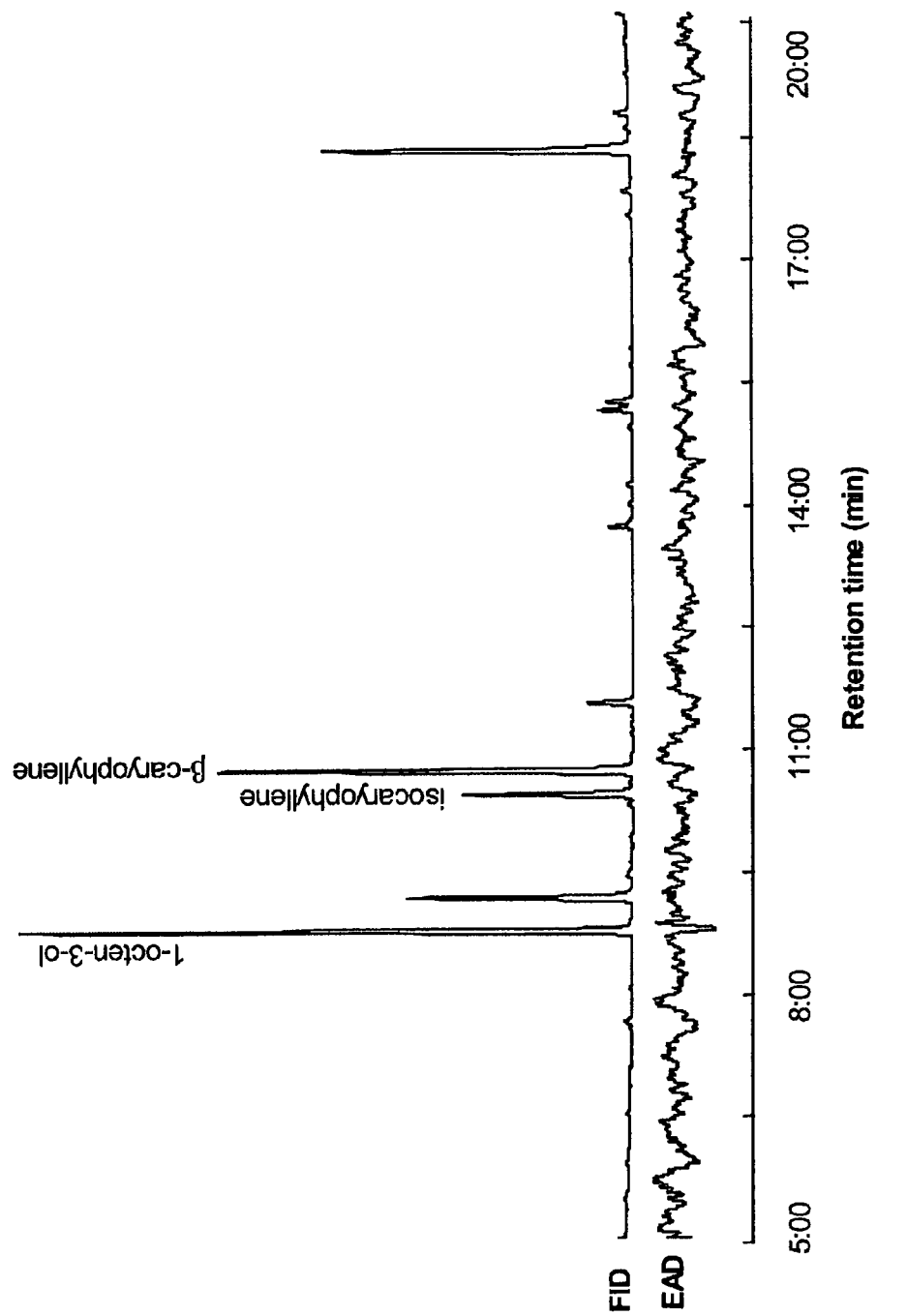
FIG. 7 shows the GC-EAD responses of the female mosquito *Culex pipiens* antenna to a synthetic mixture of 1-octen-3-ol, β-caryophyllene, and isocaryophyllene.
Figure 8:
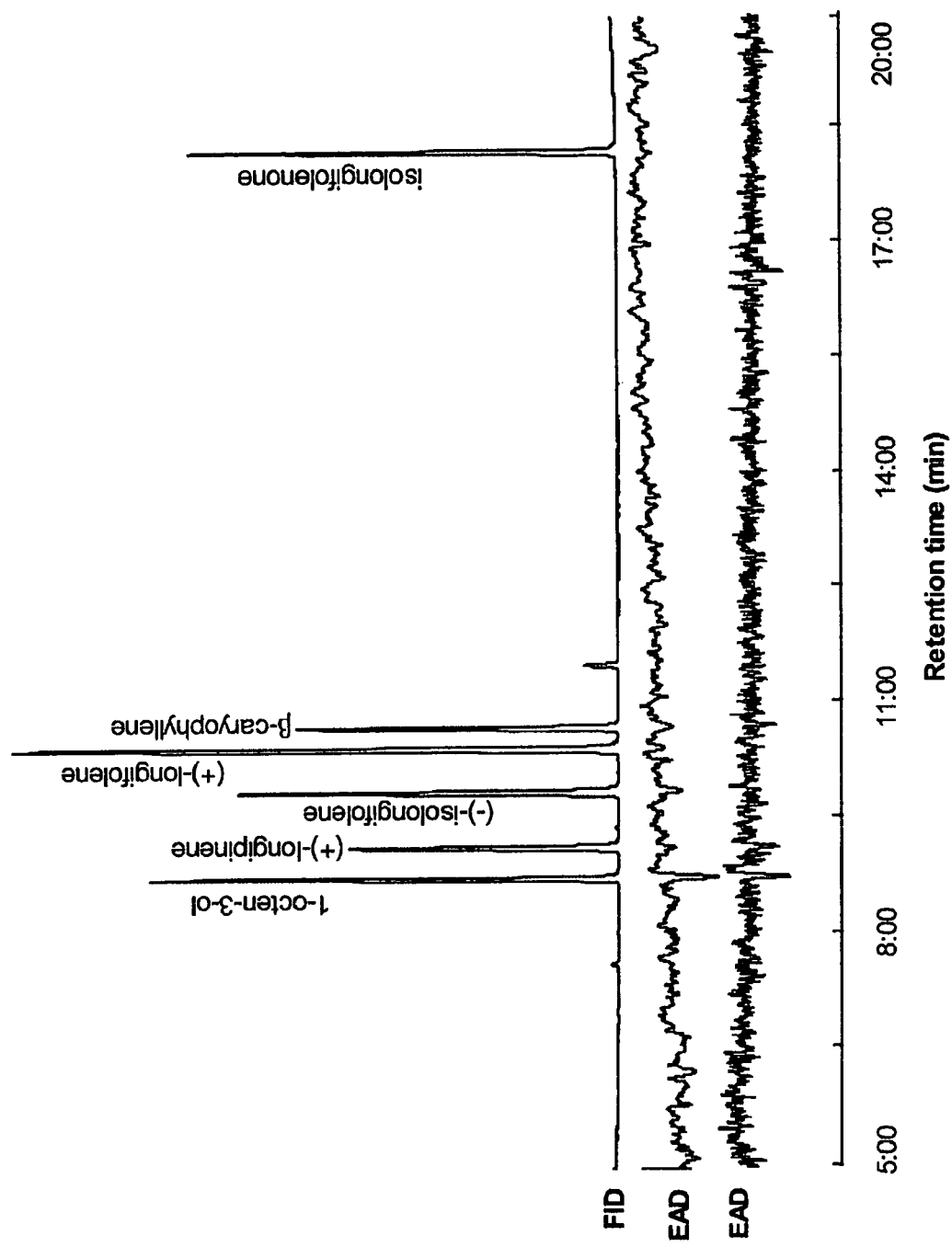
FIG. 8 shows the GC-EAD responses of the female mosquito *Culex pipiens* antenna to a synthetic mixture of 1-octen- 3-ol, (+)-longipinene, (−)-isolongifolene, (+)-longifolene, β-caryophyllene, and isolongifolenone.

As shown in FIGS. 7 and 8, the sesquiterpene hydrocarbons, (+)-longipinene, (−)-isolongifolene, (+)-longifolene, β-caryophyllene and isocaryophyllene appear to be active on female *Culex pipiens* antennae. Antennal responses were weak, but repeatable, thus are considered to be true responses.

The GC-EAD responses of female antennae of the sand fly, *Phlebotomus papatasi*, and three species of mosquitoes, *Aedes aegypti, Anopheles gambiae*, and *anopheles stephensi* were tested on a synthetic mixture of 1-octen-3-ol, six sesquiterpene hydrocarbons including (+)-longipinene, (−)-isolongifolene, (+)-longifolene, β-caryophyllene, isolongifolenone, and α-humulene, and several known insect repellents including ZE-nepetalactone, EZ-nepetalactone, with about 100 ng of each compound in the mixture. The results are shown in FIG. 9.

The GC-EAD responses of female antennae of the sand fly, *Phlebotomus papatasi*, and three species mosquitoes, *Aedes aegypti, Anopheles gambiae*, and *anopheles stephensi* were tested on a synthetic mixture of 1-octen-3-ol, linalool, β-caryophyllene oxide, isocaryophyllene, β-caryophyllene, and α-humulene, and DEET, with about 100 ng of each compound in the mixture. The results are shown in FIG. 10.

Figure 9:
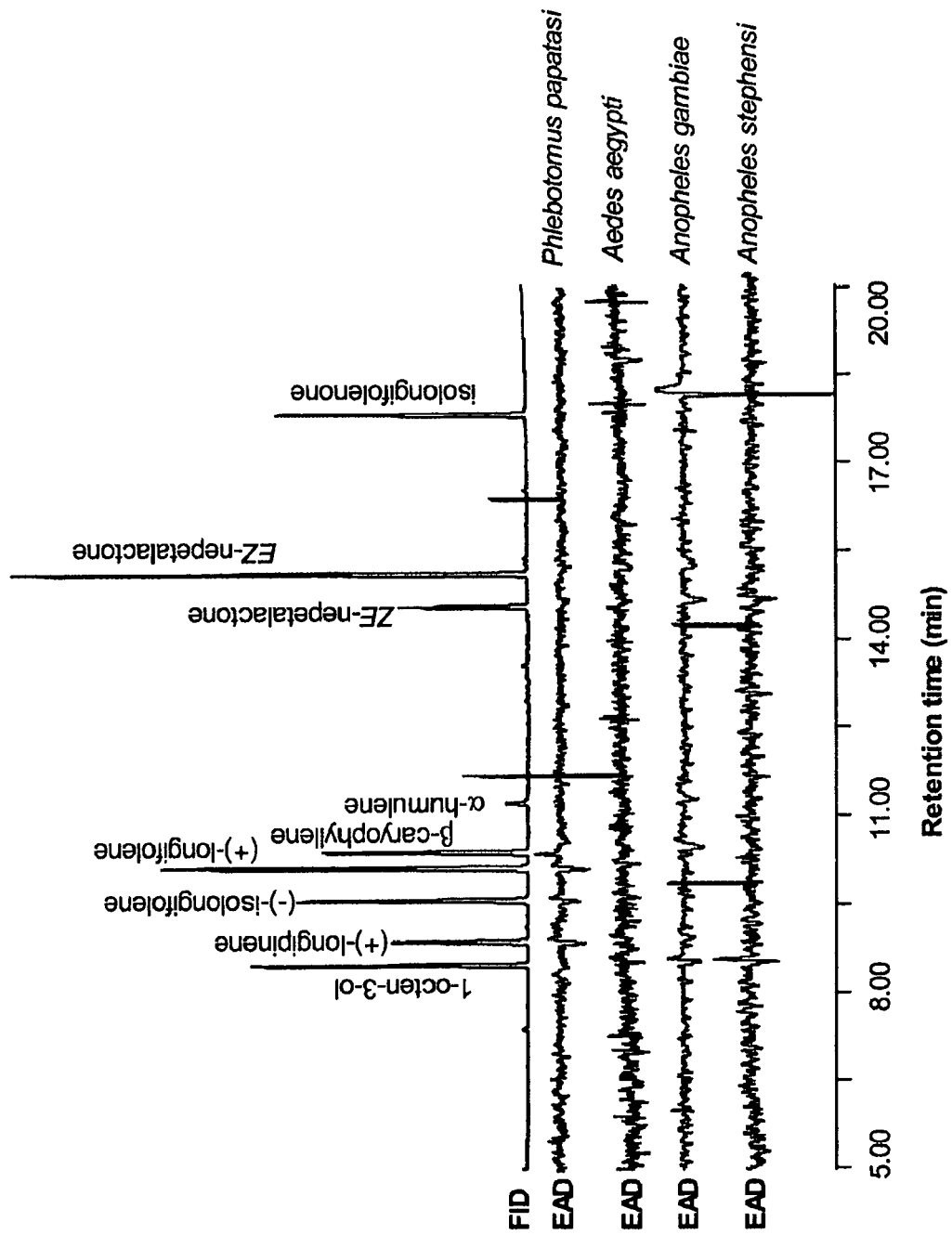
FIG. 9 shows GC-EAD responses of the sand fly and three species of mosquitoes to a synthetic mixture of 1-octen-3-ol, (+)-longipinene, (−)-isolongifolene, (+)-longifolene, β-caryophyllene, α-humulene, ZE-nepetalactone, EZ-nepetalactone, and isolongifolenone.
Figure 10:
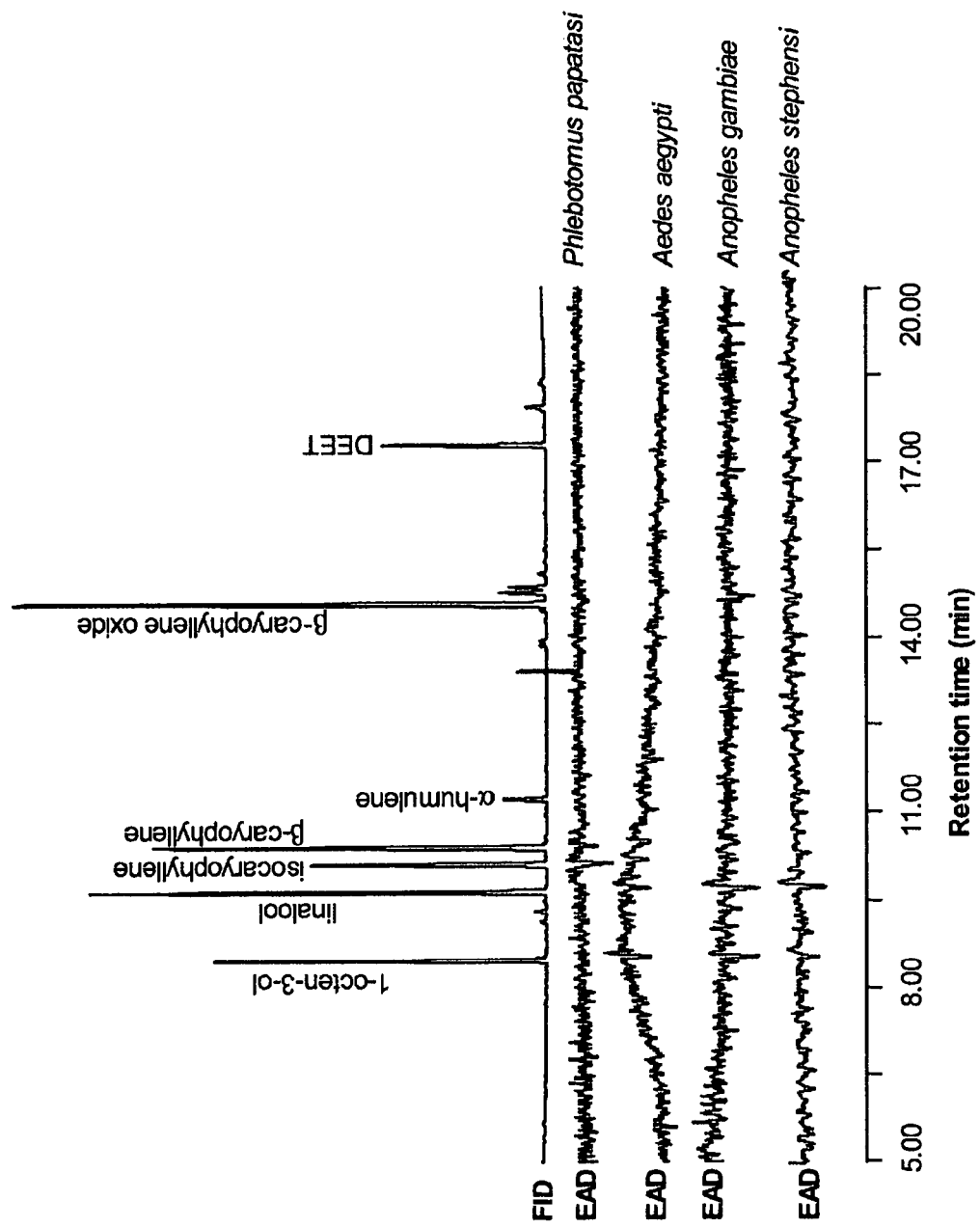
FIG. 10 shows GC-EAD responses of the sand fly, and three species of mosquitoes to a synthetic mixture of 1-octen-3-ol, linalool, isocaryophyllene, β-caryophyllene, α-humulene, caryophyllene oxide, and DEET.

As shown in FIGS. 9 and 10, the compounds β-caryophyllene, its cis-isomer isocaryophyllene, α-humulene, (+)-longipinene, (−)-isolongifolene, (+)-longifolene, β-caryophyllene oxide, and linalool appear to be antennally active on one or more of the sand fly (*Phlebotomus papatasi*) or the mosquitoes, while DEET or isolongifolenone does not appear to have elicited antennal activity at the dose tested.

Figure 11:
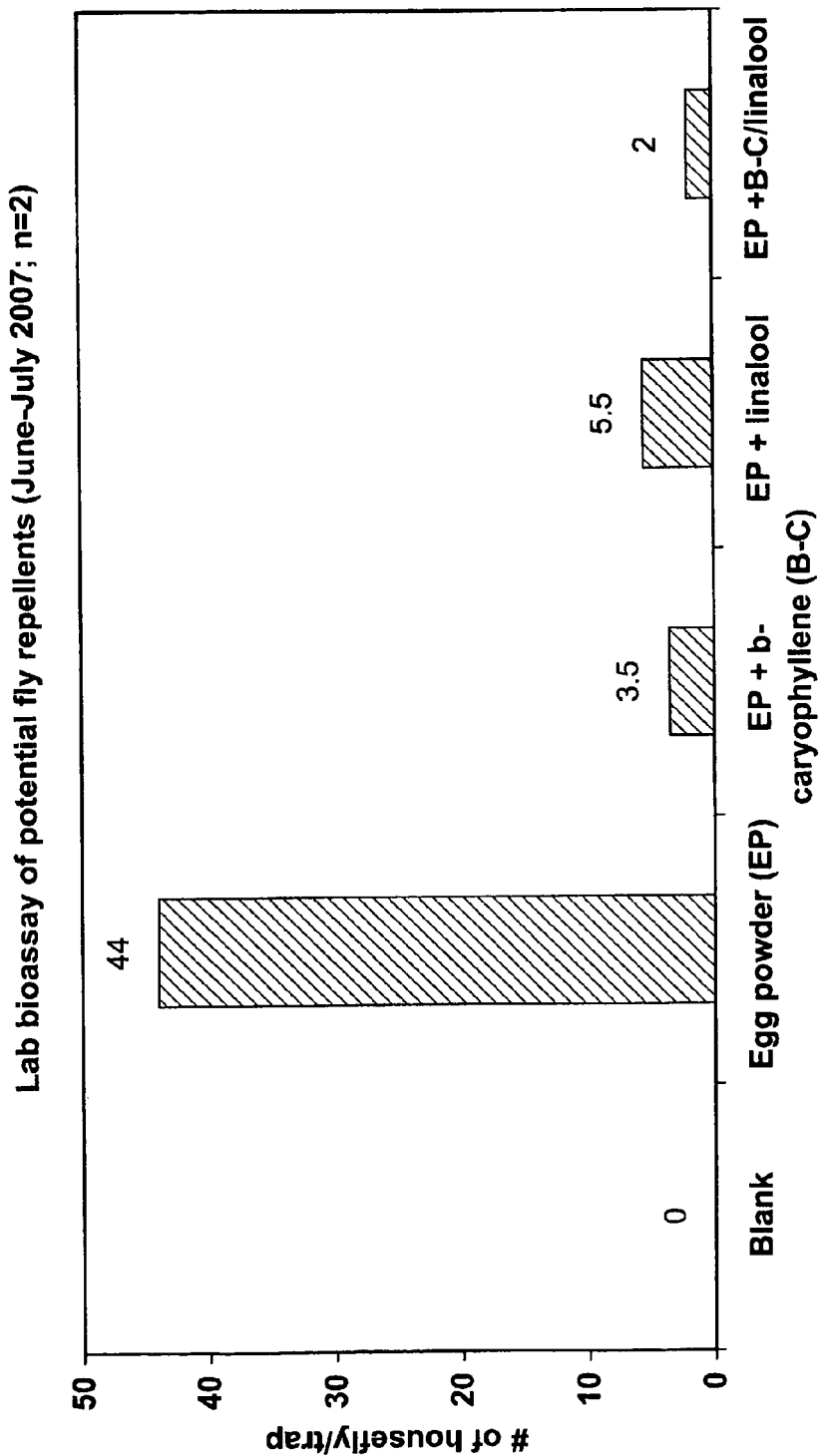
FIG. 11 shows a laboratory bioassay of the repellent effects of β-caryophyllene and linalool on the housefly with egg powder used as an attractant.
Figure 12:
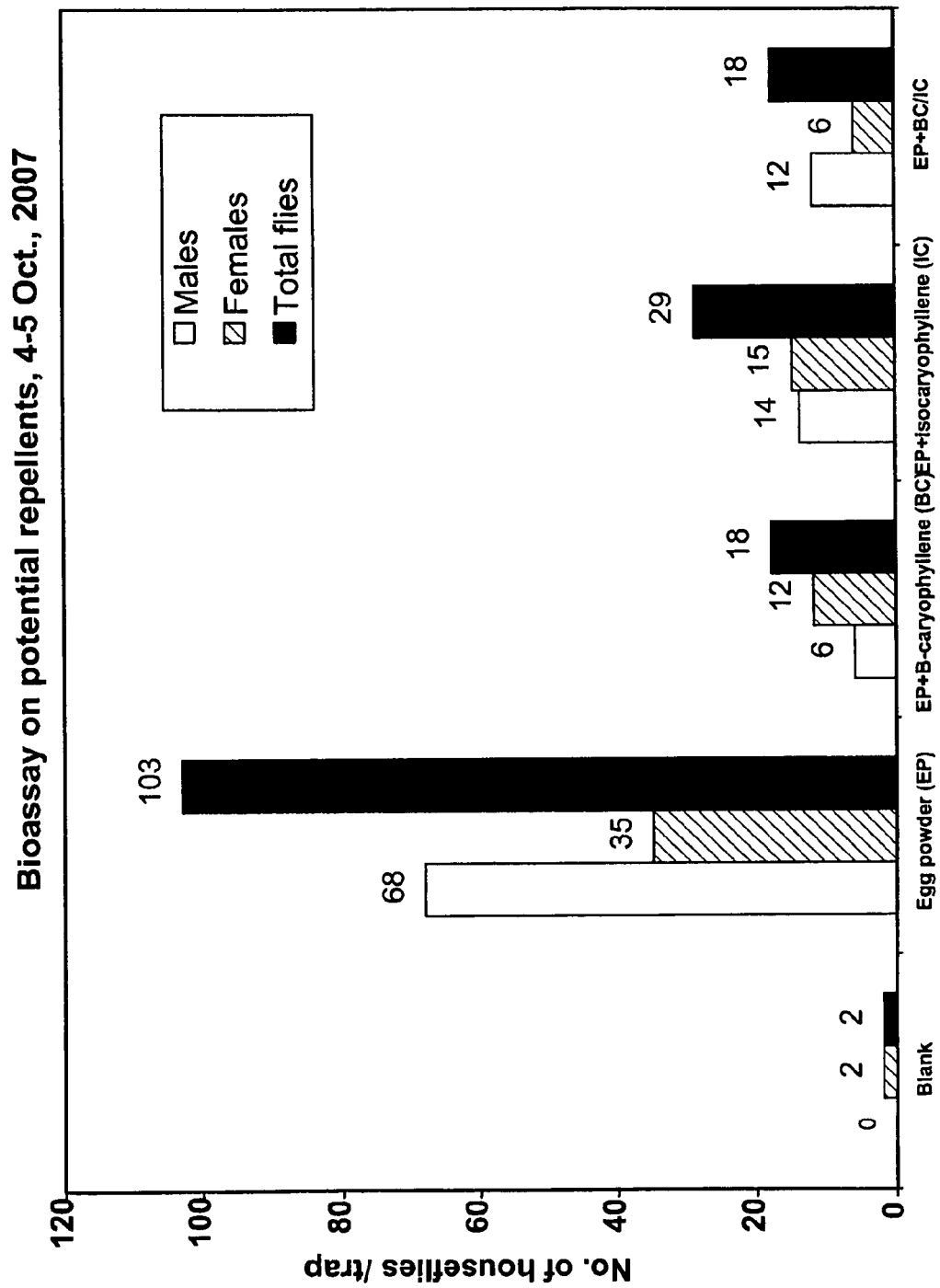
FIG. 12 shows a laboratory bioassay of the repellent effects of β-caryophyllene and isocaryophyllene on the housefly with egg powder used as an attractant.
Figure 13:
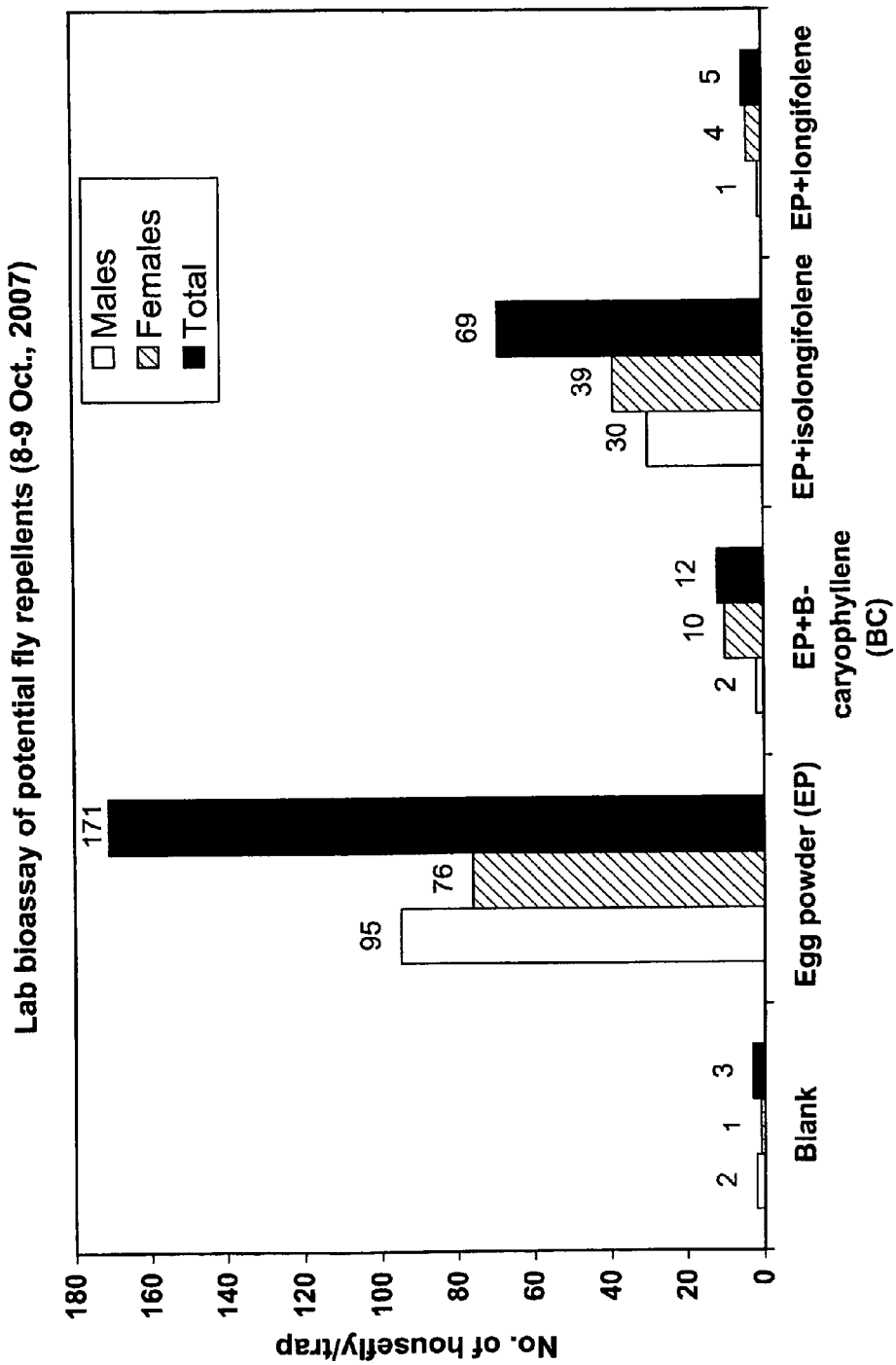
FIG. 13 shows a laboratory bioassay of the repellent effects of β-caryophyllene, (+)-longifolene, and (−)-isolongifolene on the housefly with egg powder used as an attractant.

Laboratory bioassay tests were carried out to investigate the efficacy of some of the EAD-active compounds described above to act as spatial repellents against several insects. The procedure for the bioassay tests is described in Example 2 below. Briefly stated, the bioassay included using egg powder (EP) as an attractant for flies, while the compound whose insect repellency was being tested was placed in proximity to the egg powder. In FIGS. 11-13, the bioassay was carried out on houseflies using devices known by the designation Trécé Pherocon® VI sticky traps.

FIG. 11 shows the laboratory bioassay of the spatial repellent effects of β-caryophyllene, linalool, and a mixture of β-caryophyllene and linalool. FIG. 11 shows a graph of the number of house flies per trap plotted against a blank control having no attractant or repellent, a control using only the egg powder attractant, and three combinations of egg powder with two individual repellents, and a combination of repellents. FIG. 11 demonstrates that both β-caryophyllene and linalool are effective housefly repellents. The blank control showed no attraction for flies. Using the egg powder attractant alone resulted in an average of 44 house flies per trap. The egg powder and β-caryophyllene resulted in an average of 3.5 house flies per trap. The egg powder and linalool resulted in 5.5 house flies per trap. The egg powder and combination β-caryophyllene and linalool resulted in two house flies per trap. FIG. 11 demonstrates that while both β-caryophyllene and linalool are house fly repellents, the combination appears to have a synergistic effect in repelling as evidenced by attracting the least amount of flies using the combination.

FIG. 12 is another bar graph showing results of a bioassay testing the repellency of β-caryophyllene, isocaryophyllene, and the combination. The egg powder alone attracted on average 68 male house flies per trap, and 35 females per trap. Egg powder and β-caryophyllene attracted six male house flies per trap and 12 female house flies per trap. Egg powder and isocaryophyllene attracted 14 male house flies per trap, and 15 female house flies per trap. Egg powder and a combination of β-caryophyllene and isocaryophyllene attracted 12 male house flies per trap and 6 female house flies per trap. FIG. 12 demonstrates that while both tested compounds showed repellent activities against houseflies, β-caryophyllene exhibited a stronger repelling activity against the male houseflies than the female houseflies.

Similarly, a laboratory bioassay of the spatial repellent effects of β-caryophyllene, (+)-longifolene, and (−)-isolongifolene on houseflies was carried out. FIG. 13 is a bar graph plotting the number of house flies per trap attracted for various combinations of an attractant and repellent compounds. A blank control attracted two male house flies per trap and one female house fly per trap. Egg powder alone attracted 95 male house flies and 76 female house flies. Egg powder and β-caryophyllene attracted two male house flies and 10 female house flies per trap. Egg powder and (−)-isolongifolene attracted 30 male house flies and 39 female house flies per trap. Egg powder and (+)-longifolene attracted one male house fly and 4 female house flies per trap. FIG. 13 shows that among three tested compounds, (+)-longifolene is the strongest repellent against houseflies. In addition, all three compounds exhibited stronger repelling activity against male houseflies than against female houseflies.

These laboratory bioassays demonstrated that the tested sesquiterpene hydrocarbons are effective repellents against flies. As shown in FIGS. 11-13, the EAD-active sesquiterpene hydrocarbons and derivatives, β-caryophyllene, isocaryophyllene (−)-isolongifolene, and (+)-longifolene significantly reduced the trap catches of houseflies (both sexes) by 50-95%, and in some cases, totally blocked the attraction of houseflies to the egg powder attractant.

Figure 14:
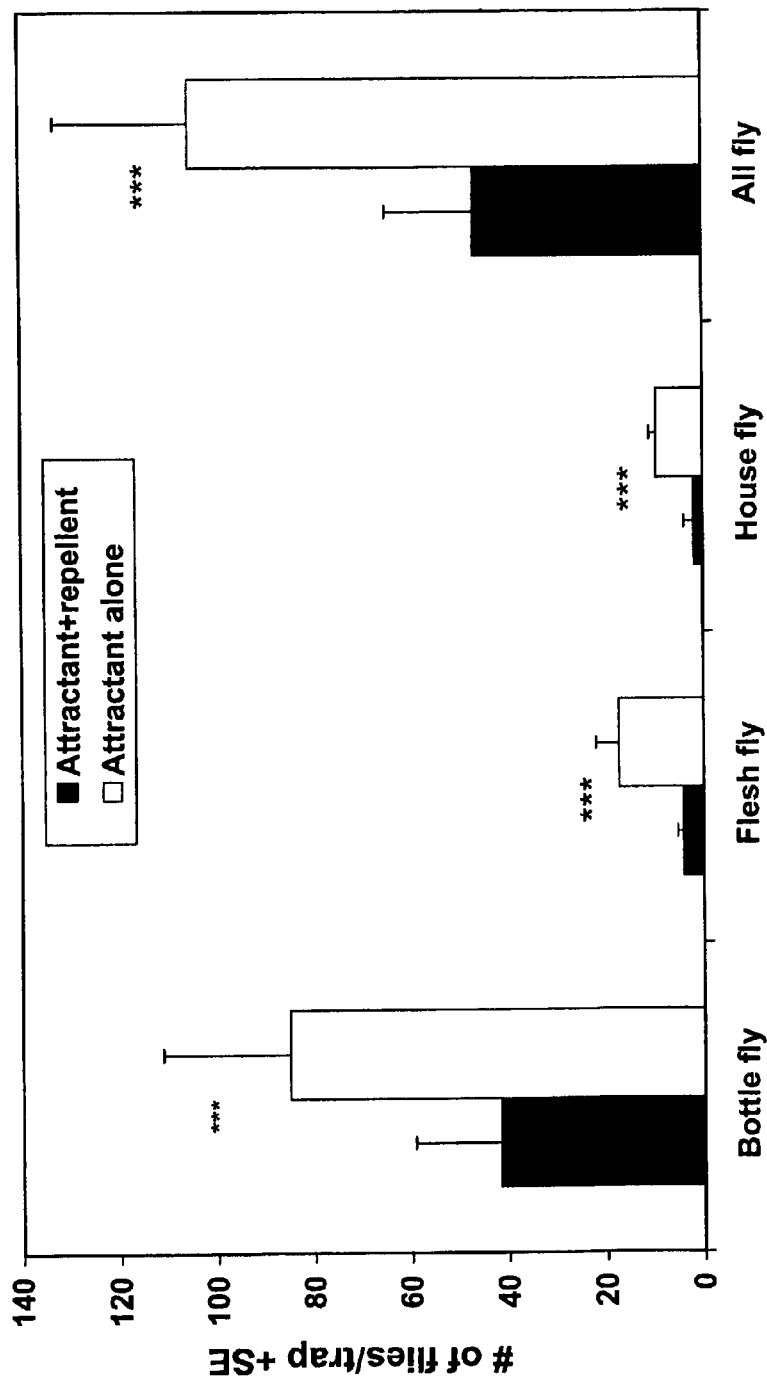
FIG. 14 shows a field bioassay of the repellent effects of β-caryophyllene on several species of flies, in which the notation (***) indicates a significant difference between the treatments at P<0.001 by pair-T test.

A field bioassay of the spatial repellent effects on three species of flies was carried out with β-caryophyllene, as described in Example 3 below. The bioassay used the commercially available fly attractant known under the designation Rescue® and a newly developed reusable prototype trap, disclosed in U.S. Pat. No. D561,297, which is incorporated herein by reference. As shown in FIG. 14, β-caryophyllene significantly reduced the trap catches of houseflies, bottle flies, and flesh flies by about 50 to about 80%.

Laboratory Y-tube behavioral bioassays as described in Example 4 were conducted to test the spatial repellent effects of clove oil, patchouli oil, β-caryophyllene, isocaryophyllene, (+)-longifolene, α-guaiene, β-caryophyllene oxide, β-caryophyllene ketone the combination of β-caryophyllene and isocaryophyllene and (+)-longifolene, on the sand fly, *Phlebotomus papatasi*, and mosquitoes, including *Aedes aegypti* and *Anopheles stephensi*. The results are shown in Table 1.

effects not only on the two mosquito species, including *Aedes Aegypti* and *Anopheles stephensi*, but also on the sand fly, *P. papatasi*. A value of P<0.05 indicates a significant repellency. The blank-blank control tests showed no differences in the number of mosquitoes or sand flies between left and right arms.

Laboratory K&D module bioassays of the topical repellent effects on mosquito species *Aedes aegypti* and *Anopheles stephensi* were carried out using clove oil, patchouli oil, α-guaiene, α-bulnesene, β-caryophyllene, isocaryophyllene, (+)-longifolene, the combination of β-caryophyllene and isocaryophyllene and (+)-longifolene, β-caryophyllene oxide, and β-caryophyllene ketone, as described in Example 5

TABLE 1

Y-tube Behavioral Bioassays With Potential Spatial Repellent Candidate Chemicals (Mixtures) Against Mosquito and Sand Fly Females

| Insect | Chemical(s) | Dispenser | Release Rate (mg/day) | Number of mosquitoes in each arm — Repellent | Blank | Bottom | $x^2$ | P | SAI* |
|---|---|---|---|---|---|---|---|---|---|
| *Aedes aegypti* | Blank | PE-Bag | 0 | 5 | 7 | 42 | 0.333 | 0.564 | 0.17 |
| | Clove Oil | PE-Bag | 10 | 4 | 31 | 12 | 20.8 | <0.0001 | 0.77 |
| | Patchouli Oil | PE-Bag | 15 | 19 | 39 | 28 | 6.9 | 0.009 | 0.34 |
| | α-Guaiene | PE-Bag | 35 | 13 | 49 | 16 | 20.9 | <0.0001 | 0.58 |
| | α-Bulnesene | PE-Bags | 60 | 11 | 35 | 24 | 12.5 | <0.0001 | 0.52 |
| | β-Caryophyllene | PE-Bag | 10 | 6 | 20 | 40 | 7.54 | 0.006 | 0.54 |
| | Isocaryophyllene | PE-Bag | 15 | 8 | 35 | 31 | 17 | <0.0001 | 0.63 |
| | (+)-Longifolene | PE-Bag | 10 | 5 | 20 | 37 | 9 | 0.003 | 0.60 |
| | β-Caryophyllene + Isocaryophyllene + (+)-Longifolene | PE-Bag | 20 | 7 | 31 | 26 | 15.2 | <0.0001 | 0.63 |
| | β-Caryophyllene Oxide | Open Cap | 1 | 15 | 38 | 26 | 9.98 | 0.002 | 0.43 |
| | β-Caryophyllene Ketone | Open Cap | 2 | 28 | 37 | 20 | 1.25 | 0.264 | 0.14 |
| *Anopheles stephensi* | Clove Oil | PE-Bag | 10 | 1 | 26 | 58 | 23.1 | <0.0001 | 0.93 |
| | Patchouli Oil | PE-Bag | 15 | 17 | 67 | 21 | 29.8 | <0.0001 | 0.60 |
| | α-Guaiene | PE-Bag | 35 | 6 | 20 | 40 | 7.54 | 0.006 | 0.54 |
| | α-Bulnesene | PE-Bags | 60 | 13 | 33 | 25 | 8.7 | 0.003 | 0.43 |
| | β-Caryophyllene | PE-Bag | 10 | 19 | 23 | 26 | 0.381 | 0.537 | 0.10 |
| | β-Caryophyllene | PE-Bag | 35 | 5 | 22 | 43 | 10.7 | 0.001 | 0.63 |
| | Isocaryophyllene | PE-Bag | 15 | 8 | 21 | 26 | 5.83 | 0.016 | 0.45 |
| | (+)-Longifolene | PE-Bag | 10 | 9 | 23 | 29 | 6.12 | 0.013 | 0.44 |
| | β-Caryophyllene + Isocaryophyllene + (+)-Longifolene | PE-Bag | 20 | 4 | 18 | 43 | 8.91 | 0.003 | 0.64 |
| | β-Caryophyllene Oxide | Open Cap | 1 | 15 | 24 | 23 | 2.08 | 0.150 | 0.23 |
| | β-Caryophyllene Ketone | Open Cap | 2 | 10 | 18 | 32 | 2.29 | 0.131 | 0.29 |
| *Phlebotomus papatasi* | Blank | PE-Bag | 0 | 33 | 35 | 42 | 0.0588 | 0.808 | 0.03 |
| | Clove Oil | PE-Bag | 10 | 8 | 47 | 7 | 27.7 | <0.0001 | 0.71 |
| | Patchouli Oil | PE-Bag | 15 | 4 | 48 | 30 | 37.2 | <0.0001 | 0.85 |
| | α-Guaiene | PE-Bag | 35 | 5 | 41 | 17 | 28.2 | <0.0001 | 0.78 |
| | β-Caryophyllene | PE-Bag | 10 | 9 | 33 | 25 | 13.7 | <0.0001 | 0.57 |
| | Isocaryophyllene | PE-Bag | 15 | 40 | 64 | 34 | 5.54 | 0.019 | 0.23 |
| | (+)-Longifolene | PE-Bag | 10 | 5 | 17 | 41 | 6.55 | 0.011 | 0.55 |
| | β-Caryophyllene + Isocaryophyllene + (+)-Longifolene | PE-Bag | 20 | 13 | 26 | 19 | 4.33 | 0.037 | 0.33 |
| | β-Caryophyllene Oxide | Open Cap | 1 | 4 | 83 | 5 | 71.7 | <0.0001 | 0.91 |
| | β-Caryophyllene Ketone | Open Cap | 2 | 20 | 29 | 23 | 1.65 | 0.199 | 0.18 |

*Spatial Activity Index (SAI) = (Nc − Nt)/(Nc + Nt); Nc is the number of females in the blank control arm, Nt is the number of females in the treatment arm. SAI is the measure of the proportion of females in the blank arm over the treatment arm after correcting for proportion of females in the blank arm; SAI varies from −1 to 1, with zero indicating no response.

As shown in Table 1, clove essential oil (ca. 10 mg/day release rate), patchouli oil (15 mg/d) and the EAD-active sesquiterpenes tested including β-caryophyllene and derivatives, isocaryophyllene, (+)-longifolene, and α-guaiene, ranging from 1 to 35 mg/d release, showed spatial repellency below. The bioassays were conducted with a six-cell in vitro K&D module system, as disclosed in Klun and Debboun, *J. Med. Entomol.* 37:177-181 (2000), loaded with an "artificial blood" (CPDA+ATP) solution. The results are listed in Table 2.

TABLE 2

K&D Module Behavioral Bioassays With Potential Topical Repellent Candidates

| Mosquitoes | Concentration ($\mu g/cm^2$) | % of biting (±SE) (N = 3)* | | | |
|---|---|---|---|---|---|
| | | Clove Oil | Patchouli Oil | α-Guaiene | α-Bulnesene |
| Aedes aegypti | 0 (blank) | 67 ± 7b | 60 ± 0c | 67 ± 7c | 93 ± 7c |
| | 10 | 7 ± 7a | 20 ± 0b | 33 ± 7b | 73 ± 7b |
| | 100 | 0 ± 0a | 0 ± 0a | 0 ± 0a | 0 ± 0a |
| | 500 | 0 ± 0a | 0 ± 0a | 0 ± 0a | 0 ± 0a |
| | 1000 | 0 ± 0a | 0 ± 0a | 0 ± 0a | 0 ± 0a |
| | 10 (DEET) | 0 ± 0a | 13 ± 13a | 7 ± 7a | 0 ± 0a |
| Anopheles stephensi | 0 (blank) | 67 ± 7c | 80 ± 12b | 60 ± 0c | 93 ± 7b |
| | 10 | 20 ± 0b | 47 ± 7b | 40 ± 0b | 87 ± 7b |
| | 100 | 0 ± 0a | 0 ± 0a | 0 ± 0a | 0 ± 0a |
| | 500 | 0 ± 0a | 0 ± 0a | 0 ± 0a | 0 ± 0a |
| | 1000 | 0 ± 0a | 0 ± 0a | 0 ± 0a | 0 ± 0a |
| | 10 (DEET) | 0 ± 0a | 13 ± 13a | 33 ± 7b | 0 ± 0a |

| Mosquitoes | Concentration ($\mu g/cm^2$) | % of biting (±SE) (N = 3)* | | | | | |
|---|---|---|---|---|---|---|---|
| | | β-Caryo-phyllene | Isocaryo-phyllene | (+)-Longifolene | β-Caryophyllene + Isocaryophyllene + (+)-Longifolene (1:1:1) | β-Caryophyllene Oxide | β-Caryophyllene Ketone |
| Aedes aegypti | 0 (blank) | 47 ± 7b | 53 ± 7c | 47 ± 7c | 47 ± 13c | | |
| | 10 | 40 ± 12b | 33 ± 7b | 53 ± 7c | 33 ± 7bc | | |
| | 100 | 33 ± 24b | 0 ± 0a | 33 ± 13bc | 47 ± 13c | | |
| | 500 | 0 ± 0a | 0 ± 0a | 0 ± 0a | 13 ± 13ab | | |
| | 1000 | 0 ± 0a | 0 ± 0a | 0 ± 0a | 0 ± 0a | | |
| | 10 (DEET) | 0 ± 0a | 0 ± 0a | 20 ± 12ab | 7 ± 7ab | | |
| | 0 (blank) | | | | | 60 ± 0c | 60 ± 0c |
| | 1 | | | | | 27 ± 7b | 20 ± 0bc |
| | 5 | | | | | 27 ± 7b | 13 ± 7ab |
| | 10 | | | | | 0 ± 0a | 7 ± 7ab |
| | 50 | | | | | 0 ± 0a | 0 ± 0a |
| | 10 (DEET) | | | | | 0 ± 0a | 7 ± 7ab |
| Anopheles stephensi | 0 (blank) | 60 ± 12c | 67 ± 7b | 53 ± 18bc | 60 ± 0b | | |
| | 10 | 47 ± 18bc | 33 ± 13b | 53 ± 7c | 67 ± 18b | | |
| | 100 | 40 ± 12bc | 7 ± 7a | 33 ± 7bc | 20 ± 12a | | |
| | 500 | 0 ± 0a | 0 ± 0a | 0 ± 0a | 7 ± 7a | | |
| | 1000 | 7 ± 7a | 0 ± 0a | 0 ± 0a | 0 ± 0a | | |
| | 10 (DEET) | 13 ± 13ab | 7 ± 7a | 27 ± 7b | 7 ± 7a | | |
| | 0 (blank) | | | | | 60 ± 12c | 67 ± 7d |
| | 1 | | | | | 27 ± 13abc | 47 ± 7cd |
| | 5 | | | | | 47 ± 7bc | 33 ± 7bc |
| | 10 | | | | | 20 ± 12ab | 20 ± 12ab |
| | 50 | | | | | 0 ± 0a | 0 ± 0a |
| | 10 (DEET) | | | | | 13 ± 7a | 7 ± 7a |

*Data in the same column with same letter, within the same species and chemical, are not significantly different (P > 0.05) by ANOVA on arcsin sqt P followed by Duncan's multiple-range test.

As shown in Table 2, over 50-60% of mosquitoes fed on the "artificial blood," for both mosquito species (*Ae. aegypti* and *An. stephensi*) in the blank control, while DEET (at 10 $\mu g/cm^2$) significantly inhibited/blocked the feeding (biting) activity. The three tested sesquiterpenes showed similar repellency/feeding deterrent patterns in a clear dose-response fashion, with lower concentrations (10-100 $\mu g/cm^2$ or less) being inactive, and repellency becoming significant and totally blocking insects at 100-500 $\mu g/cm^2$ or higher. β-caryophyllene oxide and ketone showed even stronger topical repellency on both species at similar or lower dosages as those used for DEET. Significant repellency was also found for clove and patchouli oils at about 10 mg/d release.

The sesquiterpene hydrocarbons and derivatives disclosed herein may be formulated into suitable devices or dispensers to provide a spatial repellent. The application of the compounds for spatial deterrence includes, but is not limited to, the following methods. For use as a spatial repellent, the method may include dispensing into an area, where one wants to provide such inhibiting or deterring effect, an effective amount of at least one repellent compound selected from seychellene, α-guaiene, and α-bulnesene, or a mixture thereof. One or more additional compounds selected from β-caryophyllene, isocaryophyllene, β-caryophyllene oxide, β-caryophyllene ketone, α-humulene, β-patchoulene, α-patchoulene, β-elemene, (+)-longipinene, (−)-isolongifolene, (+)-longifolene, and linalool may be used. Furthermore, clove oil or/and patchouli oil may be used together with one or more compounds selected from seychellene, α-guaiene, and α-bulnesene, to treat a desirable area for the purpose of repelling insects from the area.

The dispensing of such repellent compounds may be achieved by way of evaporation of the active compounds from a device with either controlled release or passive release. For example, the compounds can be mixed with a suitable carrier and placed inside a container for controlled release. Representative control release strategies include absorbing the compounds on a porous substrate or combining the compounds with a polymeric gel. The release devices can vary in their shapes and/or sizes to fit different settings, such as incorporating the compounds into ornaments to be inconspicuously placed in indoor or outdoor locations, or can be used for dual purposes, such as decorations having insect-repellent properties, and for use in buildings or vehicles.

In one embodiment, the repellent compounds may be dispersed by an aerosol that could be sprayed on the ground or in the air. In another embodiment, the repellent compounds may be dispersed by scattering a powdery substrate containing the repellent compounds.

The repelling of an insect of the order Diptera from a human or animal subject can include applying to a subject or to a device worn by the subject at least one repellent compound selected from a group consisting of seychellene, α-guaiene, and α-bulnesene, or a mixture thereof. Other compounds may be used together with seychellene, α-guaiene, and/or α-bulnesene to repel an insect from a human or animal subject including β-caryophyllene, isocaryophyllene, β-caryophyllene oxide, β-caryophyllene ketone, α-humulene, β-patchoulene, α-patchoulene, β-elemene, (+)-longipinene, (−)-isolongifolene, (+)-longifolene, and linalool. Additionally, seychellene, α-guaiene, and/or α-bulnesene may be used together with clove oil, patchouli oil, or both, on a human or animal subject for insect repelling purpose.

The repellent compounds may be applied to a human or animal subject in varieties of ways for insect repelling purposes. For example, an effective dose of a repellent compound or a mixture thereof may be applied directly to the skin of the subject. Alternatively, the repellent compounds may be formulated into creams, lotions, aerosols, or other suitable formulations for topical application. In addition, the repellent compounds may be absorbed on a powdery porous substrate and applied directly to the subject.

The repellent compounds or a mixture of the repellent compounds may be applied to a device worn by a human or animal subject. In one embodiment, the device may include an adsorbent substrate and the repellent compound is adsorbed on the adsorbent substrate. In one embodiment, the device may include a diffusion barrier that releases the repellent compound from the device at a predetermined rate. For example, the diffusion barrier may be a polyethylene film. In one embodiment, the repellent compound may be placed within a polyethylene film and carried by a human or animal subject.

EXAMPLES

Example 1

The following procedures were employed to test the EAD response of an insect antenna to a repellent compound. The GC-EAD technique provides an efficient tool for screening behaviorally active repellents. Several synthetic mixtures of potential insect repellent candidates, mostly sesquiterpene hydrocarbons and derivatives, were analyzed in splitless mode using a Varian CP-3800 GC equipped with a polar column (Innowax; 1.0 µm film thickness, 30 m×0.53 mm ID; J & W Scientific), and a 1:1 effluent splitter that allowed simultaneous flame ionization detection (FID) and EAD of the separated volatile compounds. Helium was used as the carrier gas, and the injector temperature was 220° C. The column temperature was 50° C. for 2 min, rising to 240° C. at 10° C./min, then held for 10 min. The outlet for the EAD was held in a humidified air stream flowing at 0.5 liter/min. over an antennal preparation. A glass capillary indifferent electrode filled with Beadle-Ephrussi Ringer, and grounded via a silver wire, was inserted into the severed insect's head with the antennae. A similar recording electrode connected to a high-impedance DC amplifier with automatic baseline drift compensation was placed in contact with the distal end of one antenna (Zhang et al., *Chemoecology*, 10:69-80 (2000)). The antennal signals were stored and analyzed on a PC equipped with a serial IDAC interface box and the program EAD ver. 2.5 (Syntech, Hilversum, The Netherlands). The compound 1-octen-3-ol (known attractant for many flies and mosquitoes) was included in most of the synthetic mixtures, as a positive control. The results of the experiments are shown in FIGS. 1-10 and described above.

Example 2

The following lab bioassay tests were employed to illustrate the efficacy of the compounds to effectively act as spatial repellents for flies. Three sets of tests were conducted in a fly testing room (23° C., 70% RH, and 12/12 (L/D) light regime illuminated by fluorescent lights). Two sets of tests were carried out using Trécé Pherocon® VI traps with sticky inserts, which were set up on poles evenly spaced on a rotating table. The traps were ca. 1 m above a table surface, and ca. 1 m apart from each other. Two grams of egg powder in a white cap (4 cm in diameter, 0.5 cm in height) used as an attractant was put on the center of the sticky insert in the sticky trap. The potential repellent candidate chemicals were loaded into polyethylene bags, and were hung under the inner roof of the traps, 1-1.5 cm above the egg powder attractant. A control had the empty white cap and blank polyethylene bag, while the positive control had only the egg powder and an empty polyethylene bag. The test table was rotated 1.5 r.p.h. (moved ⅛ of the rotation during 4 sec, and stayed in place for 5 min. before moving; thus there were 12 movements per hr., and resulted in 1.5 rotations) to reduce the positional effect. About 200-300 houseflies (2-3 days old) were released into the testing room for each test. Tests were normally run from 8:00 am to 5:00 pm, and the numbers of houseflies caught in each trap were counted after each test. The results of these tests are shown in FIGS. 11-13 and described above.

Example 3

A field trapping experiment was carried out to test the potential repellency of β-caryophyllene on different filth flies. The experiment uses a commercially available fly attractant known under the designation Rescue® and a newly developed reusable prototype trap disclosed in U.S. Design Pat. No. D561, 297 (Schneidmiller, 2008), incorporated herein by reference in its entirety. Seven pairs of such traps, one with attractant alone and the other with attractant plus the β-caryophyllene dispensed through a polyethylene bag within each pair, were set up in different locations with a suitable level of fly populations. In order to reduce the positional effect, the traps within each pair were shifted at least once before gathering counts. The results of the field trapping experiments are shown in FIG. 14 and described above.

Example 4

Clove essential oil, patchouli oil and several EAD-active compounds, as well as their partial mixtures with DEET as a positive control, were tested against a blank as a negative control in a lab Y-tube olfactometer bioassay on the two mosquito species, *Ae. Aegypti* and *An. stephensi*, and one species of sand fly, *P. papatasi*. Both the mosquitoes and the sand flies used in the study were from colonies maintained at the Walter Reed Army Institute of Research, Department of Entomology, Silver Spring, Md. This Y-tube bioassay system, equipped with $CO_2$-enriched air (ca. 1 l/min) as an attractant, was made from three clear acrylic tubes (4" diameter; 12"

length) with symmetrical 120° angles among the three tube arms; and a screen butterfly valve on the top part of the bottom releasing tube. These spatial repellency tests were carried out during 8:00 am-12:00 pm (photophase) time period for *Ae. aegypti* and 1:00-5:00 pm (shifted scotophase) time period for the species of night-flying mosquitoes and sand fly in a temperature and humidity controlled testing room (23-25° C. and 20-40% RH). Female mosquitoes or sand flies were stored at ~25-26° C., 50-89% RH, 12:12 hr. (L/D), fed with 10% sucrose solution before testing. The candidate chemical (individual or mixture) dispenser and a blank control were placed in the upper left or right arm of the Y-tube before releasing 25-40, 6 to 10 day-old female mosquitoes (or 3 to 10 day-old sand flies) into the bottom tube via a small hole. After a 30-60 sec acclimation period, the butterfly screen valve (door) on the top of the bottom tube was opened. After 10 min., the valve was closed and the numbers of mosquitoes or sand flies in each arm (including the bottom tube) were counted. In order to minimize the position effect, the same experiment was repeated once with the treatment and blank control arms shifted using a new (clean) Y-tube olfactometer and a new batch of mosquitoes/sand flies. Data from these two replicates were pooled for $\chi 2$ goodness of fit test (df=1) between the treatment and blank control. The results of the bioassay are shown in Table 1 above.

Example 5

Clove essential oil, patchouli oil, and EAD-active potential repellents, β-caryophyllene, isocaryophyllene, (+)-longifolene, and their 1:1:1 mixture, plus α-guaiene, caryophyllene oxide, and a β-caryophyllene ketone, were tested using the six-cell in vitro K&D module system (Klun and Debboun, *J. Med. Entomol.* 37:177-181 (2000)) loaded with an "artificial blood" (CPDA+ATP) solution on both *Ae. aegypti* and *An. stephensi* in a dose-response fashion. The K&D in vitro assay system has three components: (1) a Plexiglas™ 29.7 cm.×7.1 cm K&D module composed of six adjacent cells, each designed to hold mosquitoes and each having a rectangular 3×4 cm floor hole that is opened and closed by a sliding door; (2) a Plexiglas™ six-well 29.7 cm×7.1 cm water waterbath warmed (38° C.) reservoir with six 3×4 cm wells designed to match the sliding-door openings of the K&D module base and to contain 6 mL warmed "artificial blood" wells covered with a collagen membrane; and (3) a 29.7 cm×7.1 cm'0.4 cm Teflon® separator having six rectangular openings like the K&D module. The K&D module was connected to a constant temperature water circulator at 38° C. The cells were covered with an Edicol collagen membrane strip. Nylon organdy strips with ink cell patterns were numbered and randomly treated with five dilutions of the tested chemical in ethanol (ethanol alone as blank control), plus DEET (ca. 10 μg/cm$^2$) as a positive control. This treated nylon organdy strip was placed on top of the collagen membrane. The upper section of the K & D module with the six cells each containing 5 mosquitoes (5-10 d old, starved for 24 hr before testing) was placed on top of the nylon strip. The doors to the cells were slid open so the mosquitoes could be free to feed on the "artificial blood" via the collagen membrane if they were hungry. The experiments were allowed to run for 3 minutes, and the number of mosquitoes feeding (biting) in each cell was recorded. After each experiment, the nylon and collagen strips were removed. The CPDA+ATP solution was removed and allowed to dry prior to starting the next experiment. The experiments on each chemical and each mosquito species were run three times before the bottom section with circulated water was cleaned prior to use again. The results are shown in Table 2 above.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for repelling *phlebotomus papatasi* from an area, comprising treating the area with an isolated form of α-guaiene, wherein the *phlebotomus papatasi* is repelled.

2. The method of claim 1, further comprising treating the area with one or more compounds selected from the group consisting of β-caryophyllene, isocaryophyllene, β-caryophyllene oxide, β-caryophyllene ketone, α-humulene, β-patchoulene, α-patchoulene, β-elemene, (+)-longipinene, (−)-isolongifolene, (+)-longifolene, seychellene, α-bulnesene, and linalool.

3. The method of claim 1, further comprising treating the area with clove oil, patchouli oil, or a mixture thereof.

4. The method of claim 1, comprising treating the area with an aerosol carrying the isolated form of alpha-guaiene.

5. The method of claim 1, comprising treating the area with a powdery substrate carrying the isolated form of alpha-guainene.

* * * * *